US008442630B2

(12) United States Patent
Saba

(10) Patent No.: US 8,442,630 B2
(45) Date of Patent: May 14, 2013

(54) AUTOMATED ASSESSMENT OF ATRIOVENTRICULAR AND VENTRICULOATRIAL CONDUCTION

(75) Inventor: Samir F. Saba, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1188 days.

(21) Appl. No.: 12/244,367

(22) Filed: Oct. 2, 2008

(65) Prior Publication Data

US 2009/0143832 A1 Jun. 4, 2009

Related U.S. Application Data

(60) Provisional application No. 60/998,147, filed on Oct. 9, 2007.

(51) Int. Cl.
*A61N 1/39* (2006.01)
(52) U.S. Cl.
USPC .................................. 607/4; 607/17; 607/9
(58) Field of Classification Search .......... 607/9, 4, 607/17
See application file for complete search history.

(56) References Cited

U.S. PATENT DOCUMENTS

| 5,143,089 | A | 9/1992 | Alt | 607/121 |
| 5,713,930 | A * | 2/1998 | van der Veen et al. | 607/25 |
| 6,076,014 | A | 6/2000 | Alt | 607/4 |
| 6,256,537 | B1 | 7/2001 | Stoop et al. | 607/14 |
| 6,611,713 | B2 | 8/2003 | Schauerte | 607/14 |
| 2001/0020136 | A1 | 9/2001 | Sweeney et al. | 600/515 |
| 2002/0120301 | A1 | 8/2002 | Levine et al. | 607/9 |
| 2003/0078627 | A1 | 4/2003 | Casavant et al. | 607/9 |

OTHER PUBLICATIONS

Barold et al., "Prospective Evaluation of New and Old Criteria to Discriminate Between Supraventricular and Ventricular Tachycardia in Implantable Defibrillators", *Pacing Clin Electrophysiol.*, 21:1347-1355 (1998).
Buxton et al., "Current Approaches to Evaluation and Management of Patients With Ventricular Arrhythmias", *Med Health R I*, 84(2):58-62 (2001).
Finelli et al., "Effects of Increased Heart Rate and Sympathetic Tone on Intraventricular Electrogram Morphology", *Am J Cardiol.* 68:1321-1328 (1991).
Gold et al., "A New Defibrillator Discrimination Algorithm Utilizing Electrogram Morphology Analysis", *Pacing Clin Electrophysiol*, 22:179-182 (1999).
Lampert et al., "Management of Arrhythmias", *Clin Geriatr Med*, 16(3):593-618 (2000).
McAlister et al., "Atrial Electrogram Analysis: Antegrade Versus Retrograde", *PACE* 11:1703-1707 (1988).

(Continued)

*Primary Examiner* — Nicole F Lavert
*Assistant Examiner* — Alyssa Alter
(74) *Attorney, Agent, or Firm* — Medlen & Carroll, LLP

(57) ABSTRACT

A method discriminates between ventricular arrhythmia and supraventricular arrhythmia by determining the direction of an electrical signal conducted through the atrioventricular node. An implantable cardiac defibrillator provides atrioventricular and ventriculoatrial pacing bursts to determine if an arrhythmia with a 1:1 atrial to ventricular relationship is due to ventricular tachycardia or supraventricular tachycardia. This discrimination capability reduces the incidence of inappropriate shocks from dual-chamber implantable cardiac defibrillators to near zero and provides a method to differentially diagnose supraventricular tachycardia from ventricular tachycardia.

4 Claims, 15 Drawing Sheets

OTHER PUBLICATIONS

Pannizo et al., "Discrimination of Antegrade and Retrograde Atrial Depolarization by Electrogram Analysis", *Am Heart J.* 112:780-786 (1986).

Ross et al., "The Effect of Exercise on the Atrial Electrogram Voltage in Young Patients", *PACE*, 14:2092-2097 (1991).

Schaumann et al., "Enhanced Detection Criteria in Implantable Cardioverter-Defibrillator to Avoid Inappropriate Therapy", *Am J Cardiol.*, 78:42-50 (1996).

Tanaka S., "An Overview of Fifth-Generation Implantable Cardioverter Defibrillator", *Ann Thorac Cardiovasc Surg.*, 4:303-311 (1998).

Thompson et al., "Ventriculoatrial Conduction Metrics for Classification of Ventricular Tachycardia With 1:1 Retrograde Conduction in Dual-Chamber Sensing Implantable Cardioverter Defibrillators ", *J Electrocardiol.*, 31:152-156 (1988).

Throne et al., "Discrimination of Retrograde From Antegrade Atrial Activation Using Intracardiac Electrogram Waveform Analysis", *Pacing Clin Electrophysiol.*, 12:1622-1630 (1989).

Timmis et al., "Discrimination of Antegrade From Retrograde Atrial Electrograms for Physiologic Pacing", *PACE* 11:130-140 (1988).

Wainwright et al., "Ideal Atrial Lead Positioning to Detect Retrograde Atrial Depolarization by Digitization and Slope Analysis of the Atrial Electrogram", *PACE* 7:1152-1158 (1984).

Woodroofe M., *Probability With Applications*, McGraw-Hill, New York. pp. 229-239 (1975).

* cited by examiner

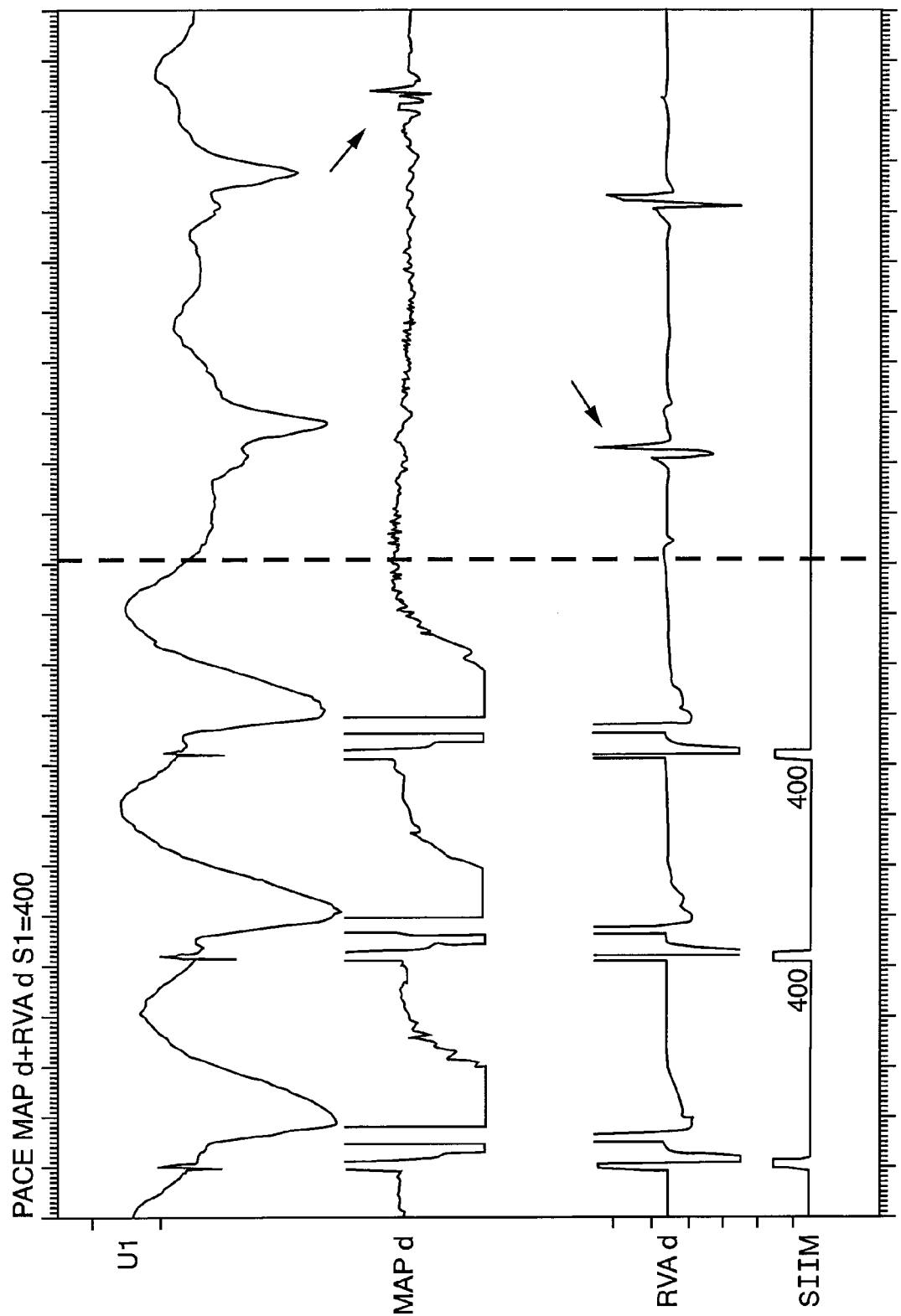

Automated Update of Minimum VAW

AUTOMATED ASSESSMENT OF ATRIOVENTRICULAR AND VENTRICULOATRIAL CONDUCTION

FIELD OF INVENTION

This invention relates to the identification and detection of abnormal heart rhythm occurring in either the supraventricular or ventricular cardiac regions. Specifically, this invention relates to a novel method of analysis to discriminate between supraventricular tachycardia and ventricular arrhythmia. More specifically, this invention relates to an implantable cardiac defibrillator device controlled by a novel method of analysis to discriminate between supraventricular tachycardia and ventricular arrhythmia.

BACKGROUND

Identifying the mechanism of an arrhythmia based on its intracardiac electrograms has become a common challenge to both implantable cardiac defibrillators (ICDs) and the physicians taking care of patients with ICDs. These devices, which are primarily designed to deliver therapy for life-threatening ventricular arrhythmia, frequently deliver inappropriate shocks for a supraventricular tachycardia (SVT). These inappropriate shocks constitute a significant source of physical and emotional distress for patients, cause early ICD battery depletions, and generate a huge financial burden on the health system.

Inappropriate electroshocks from ICDs constitute a significant source of physical and emotional distress on the patients and an unnecessary expense for the health system. Early generations of ICDs operated with an incidence of inappropriate electroshocks as high as 20 to 40%. Tanaka S., An Overview Of Fifth-Generation Implantable Cardioverter Defibrillator, Ann Thorac Cardiovasc Surg., 4:303 311 (1998). Following the introduction of dual-chamber ICDs, however, the overall success for delivering appropriate electroshocks increased to 86 to 100%, while the successful incidence for the treatment of ventricular tachycardias (VT) reached 97 to 100%.

The incidence of inappropriate electroshocks in response to a SVT however, remains a problem. This problem is especially severe for discriminating between a SVT having 1:1 antegrade conduction and a VT having 1:1 retrograde conduction. Thompson et al., Ventriculoatrial Conduction Metrics For Classification Of Ventricular Tachycardia With 1:1 Retrograde Conduction In Dual-Chamber Sensing Implantable Cardioverter Defibrillators, J Electrocardiol., 31:152 156 (1988)

The ability to reduce or avoid all inappropriate electroshocks from ICDs would have a beneficial effect on the physical and emotional state of patients with defibrillators as well as reduce the cost of health care. Clearly, what is needed in the art is a method and a device to prevent the misinterpretation of cardiac electrical signals and avoid the delivery of inappropriate electroshocks. An improved algorithm, based on a patient's baseline cardiac conduction profile as well as automatic updates of that profile, to discriminate between SVT and VT is therefore required.

SUMMARY

This invention relates to the identification and detection of abnormal heart rhythm occurring in either the supraventricular or ventricular cardiac regions. In one embodiment, the present invention contemplates a novel method of analysis to discriminate between SVT and VT. In another embodiment, the present invention contemplates a new ICD device controlled by a novel method of analysis that discriminates between SVT and VT.

One embodiment of the present invention contemplates a method comprising the steps of: a) providing, under conditions so as to generate ventricular electrical signals: i) a first set of atrial pacing bursts having a first cycle length; and ii) a second set of atrial pacing bursts, wherein said second atrial pacing bursts have a second cycle length; and b) detecting said ventricular electrical signals generated in response to said second set of atrial pacing bursts, wherein said second atrial pacing burst cycle length is shorter than said first atrial pacing burst cycle length; c) repeating step b) until said ventricular electrical signals are not detected, wherein the penultimate second atrial pacing burst establishes a minimum atrioventricular cycle length value. In one embodiment said minimum atrioventricular cycle length comprises an Atrioventricular Wenckebach cycle length. In another embodiment the method further comprises step (d) storing a basal atrioventricular cycle length value in a microprocessor. In another embodiment the method further comprises replacing said basal atrioventricular cycle length value with said minimum atrioventricular cycle length value. In yet another embodiment said microprocessor is integrated within a pacemaker/defibrillator device.

One embodiment of the present invention contemplates a method comprising the steps of: a) providing, under conditions so as to generate atrial electrical signals: i) a first set of ventricular pacing bursts having a first cycle length; and, ii) a second set of ventricular pacing bursts, wherein said second ventricular pacing bursts have a second cycle length; b) detecting said atrial electrical signals generated in response to said second set of ventricular pacing bursts, wherein said second ventricular pacing burst cycle length is shorter than said first ventricular pacing burst cycle length; c) repeating step b) until said atrial electrical signals are not detected, wherein the penultimate second ventricular pacing burst establishes a minimum ventriculoatrial cycle length value. In one embodiment said minimum ventriculoatrial cycle length comprises a Ventriculoatrial Wenckebach cycle length. In another embodiment the method further comprises step d) storing a basal ventriculoatrial cycle length value in a microprocessor. In another embodiment the method further comprises replacing said stored ventriculoatrial cycle length value with said minimum ventriculoatrial cycle length value. In yet another embodiment said microprocessor is integrated within a pacemaker/defibrillator device.

One embodiment of the present invention contemplates a method comprising the steps of: a) providing: i) a patient diagnosed with a cardiac arrhythmia, said arrhythmia having a cycle length; ii) a microprocessor comprising an atrioventricular cycle length value and a ventriculoatrial cycle length value, wherein said microprocessor is configured to receive said atrioventricular conduction signal and a ventriculoatrial conduction signal; b) determining whether said atrioventricular conduction signal and said ventriculoatrial conduction signal are present. In one embodiment the method further comprises identifying said arrhythmia cycle length when said atrioventricular conduction signal and said ventriculoatrial conduction signal have a 1:1 ratio. In one embodiment the absence of said atrioventricular conduction signal diagnoses a ventricular tachycardia. In another embodiment the absence of said ventriculoatrial conduction signal diagnoses a supraventricular tachycardia. In yet another embodiment said arrhythmia cycle length being less than said atrioventricular cycle length diagnoses a ventricular tachycardia. In yet another embodiment said arrhythmia cycle length being less than said ventriculoatrial cycle length diagnoses a supraventricular tachycardia. In one embodiment said arrhythmia cycle length being greater than said atrioventricular cycle length but less than said ventriculoatrial cycle length diagnoses a supraventricular tachycardia.

One embodiment of the present invention contemplates a method comprising the steps of: a) providing a patient comprising atrial leads and ventricular leads, wherein said leads are connected to a pacemaker/defibrillator device; b) sending a pacing burst signal to said atrial leads by said pacemaker/defibrillator; c) sending a pacing burst signal to said ventricular leads by said pacemaker/defibrillator; d) detecting an earliest arriving ventricular electrical signal following said atrial pacing burst signal under conditions that determine a minimum atrioventricular cycle length value; and e) detecting an earliest arriving atrial electrical signal following said ventricular pacing burst signal under conditions that determine a minimum ventriculoatrial cycle length value. In one embodiment said patient further comprises an arrhythmia when said ventricular electrical signal and said atrial pacing burst signal have a 1:1 ratio. In one embodiment said patient further comprises an arrhythmia when said atrial electrical signal and said ventricular pacing burst signal have a 1:1 ratio.

One embodiment of the present invention contemplates a device comprising: a) a defibrillator element comprising a microprocessor, wherein said microprocessor is capable of comparing a stored cardiac cycle length with an input cardiac cycle length; b) a pacemaker element connected to said defibrillator element; and c) a plurality of atrial and ventricular sensing leads connected to said pacemaker, wherein said leads provide said input cardiac cycle length to said microprocessor. In one embodiment said stored cardiac cycle length comprises an atrioventricular cycle length value. In another embodiment said stored cardiac cycle length comprises a ventriculoatrial cycle length value. In another embodiment said input value comprises a minimum atrioventricular cycle length value. In yet another embodiment said input value comprises a minimum ventriculoatrial cycle length value.

One embodiment of the present invention contemplates a method for using an arrhythmia discrimination algorithm that discriminates between VT and/or SVT, comprising the steps of: a) pacing the atria and ventricles of a patient with pacing bursts; b) determining the minimum AVW cycle length of an earliest arriving electrical signal in the ventricles following said atrial pacing; c) determining the minimum VAW cycle length of an earliest arriving electrical signal in the atria following said ventricular pacing; and d) detecting an arrhythmia with a 1:1 atrial to ventricular relationship. In one embodiment, an operator manually enters information regarding the patient's baseline AV and VA conduction status. In another embodiment, the minimum AVW and VAW cycle lengths are updated automatically. In yet another embodiment, the update occurs when the patient is at an elevated sympathetic state. In one embodiment, a patient lacking AV conduction is diagnosed as having VT. In another embodiment, a patient lacking VA conduction is diagnosed as having SVT. In yet another embodiment, the cycle length of an arrhythmia is determined in a patient with AV conduction. In one embodiment, the patient is diagnosed as having VT if the cycle length of said arrhythmia is less than the minimum AVW cycle length. In another embodiment, the cycle length of the arrhythmia is determined in a patient with VA conduction. In yet another embodiment, the patient is diagnosed as having SVT if the cycle length of said arrhythmia is less than the minimum VAW cycle length. In one embodiment, the patient is diagnosed as having SVT if the cycle length of said arrhythmia is greater than the minimum AVW cycle length but is less than the minimum VAW cycle length.

One embodiment of the present invention contemplates a device, comprising: a) an implantable pacemaker element; b) an implantable defibrillator element connected to said pacemaker element, wherein said defibrillator element or said pacemaker element comprises a microprocessor with an algorithm capable of discriminating an arrhythmia; and c) a plurality of atrial and ventricular pacing leads connected to said pacemaker element, wherein said pacing leads are configured for simultaneous activation. In one embodiment, the device further comprises a plurality of atrial and ventricular defibrillation leads connected to said defibrillator element. In another embodiment, the device further comprises a plurality of atrial and ventricular sensing leads connected to said pacemaker element. In yet another embodiment, the pacemaker element further comprises a storage memory connected to said sensing leads. In one embodiment, the device is capable of detecting an earliest arriving electrical signal. In one embodiment, the algorithm determines the minimum AVW cycle length of an earliest arriving electrical signal in the ventricles following pacing of the atria, and the minimum VAW cycle length of an earliest arriving electrical signal in the atria following pacing of the ventricles. In another embodiment, the algorithm identifies a patient lacking AV conduction as having VT when said computer detects an arrhythmia exhibiting a 1:1 atrial to ventricular relationship. In yet another embodiment, the algorithm identifies a patient lacking VA conduction as having SVT when said computer detects an arrhythmia exhibiting a 1:1 atrial to ventricular relationship. In one embodiment, the algorithm identifies a patient with AV conduction as having VT if the cycle length of an arrhythmia of an arrhythmia exhibiting a 1:1 atrial to ventricular relationship is less than the minimum AVW cycle length. In another embodiment, the algorithm identifies a patient with VA conduction as having SVT if the cycle length of an arrhythmia exhibiting a 1:1 atrial to ventricular relationship is less than the minimum VAW cycle length. In yet another embodiment, the algorithm identifies a patient with AV conduction as having SVT if the cycle length of said arrhythmia exhibiting a 1:1 atrial to ventricular relationship is greater than the minimum AVW cycle length but is less than the minimum VAW cycle length. In one embodiment, the algorithm automatically enters said minimum AVW cycle length and/or minimum VAW cycle length into said microprocessor. In yet another embodiment, the algorithm automatically enters said minimum AVW cycle length and/or minimum VAW cycle length into said microprocessor when a patient is at an elevated sympathetic state.

One embodiment of the present invention contemplates a method of discriminating between ventricular tachycardia or supraventricular tachycardia, comprising the steps of: a) pacing a first location, further comprising the steps of: i) generating a first electrical signal at said first location; ii) detecting said first electrical signal at a second location; and iii) determining the minimum cycle length of said first electrical signal arriving at said second location; b) pacing said second location, further comprising the steps of: i) generating a second electrical signal at said second location; ii) detecting said second electrical signal at said first location; and iii) determining the minimum cycle length of said second electrical signal arriving at said first location; c) detecting an arrhythmia with a 1:1 first location to second location relationship; d) determining the cycle length of said arrhythmia; e) establishing if conduction from said first location to said second location is possible; and f) establishing if conduction from said second location to said first location is possible. In one embodiment, the minimum cycle length of said first electrical signal and said second electrical signal are updated automatically. In another embodiment, the update occurs during a period in which the rate of electrical activity is elevated. In another embodiment, ventricular tachycardia is diagnosed if conduction from said first location to said second location is not possible. In yet another embodiment, supraventricular tachycardia is diagnosed if conduction from said second location to said first location is not possible. In one embodiment, ventricular tachycardia is diagnosed if conduction from said first location to said second location is possible and if the cycle length of said arrhythmia is less than minimum the minimum cycle length of said first electrical signal arriving at said second location. In another embodiment, supraventricular tachycardia is diagnosed if conduction from said second location to said first location is possible and if the cycle length of said arrhythmia is less than minimum the minimum cycle length of said second electrical signal arriving at said first location. In yet another embodiment, supraventricular tachycardia is diagnosed if conduction from said first location to said second location is possible and if the cycle length of said arrhythmia is greater than the minimum cycle length of said first electrical signal arriving at said second location, but is less than the cycle length of said second electrical signal arriving at said first location.

One embodiment of the present invention contemplates a method for automatically updating a discrimination algorithm, comprising the steps of a) monitoring an intrinsic heart rate; b) storing a maximum intrinsic heart rate; c) pacing a first location, further comprising the steps of: i) generating a first electrical signal at said first location; ii) detecting said first electrical signal at a second location; and iii) determining the minimum cycle length of said first electrical signal arriving at said second location; d) pacing said second location, further comprising the steps of: i) generating a second electrical signal at said second location; ii) detecting said second electrical signal at said first location; and iii) determining the minimum cycle length of said second electrical signal arriving at said first location; e) updating the stored maximum intrinsic heart rate if said monitor detects an intrinsic heart rate greater than said stored maximum intrinsic heart rate; e) updating the minimum cycle length of said first electrical signal arriving at said second location; and f) updating the minimum cycle length of said second electrical signal arriving at said first location. In one embodiment, updating the minimum cycle length of said first electrical signal arriving at said second location comprises the steps of: a) pacing said first location, further comprising the steps of: i) generating an electrical signal at said first location, wherein the cycle length of said electrical signal is less than the minimum cycle length of said first electrical signal arriving at said second location; ii) detecting said electrical signal at said second location; and iii) determining if the cycle length of said electrical signal is less than the minimum cycle length of said first electrical signal arriving at said second location. In another embodiment, updating the minimum cycle length of said second electrical signal arriving at said first location comprises the steps of: a) pacing said second location, further comprising the steps of: i) generating an electrical signal at said second location, wherein the cycle length of said electrical signal is less than the minimum cycle length of said second electrical signal arriving at said first location; ii) detecting said electrical signal at said first location; and iii) determining if the cycle length of said electrical signal is less than the minimum cycle length of said second electrical signal arriving at said first location.

One embodiment of the present invention contemplates a method for discriminating between VT and SVT, comprising: a) an electrocardiogram array; b) a plurality of sensing leads configured for atrial and ventricular sensing; c) a plurality of pacing leads configured for atrial and ventricular pacing; d) a computer configured to receive electrical signals from said sensing and pacing leads; e) an arrhythmia discrimination algorithm; and f) a microprocessor for executing said algorithm. In one embodiment, the algorithm determines the minimum AVW cycle length of an earliest arriving electrical signal in the ventricles following pacing of the atria, and the minimum VAW cycle length of an earliest arriving electrical signal in the atria following pacing of the ventricles. In another embodiment, the algorithm identifies a patient lacking AV conduction as having VT when said computer detects an arrhythmia exhibiting a 1:1 atrial to ventricular relationship. In yet another embodiment, the said algorithm identifies a patient lacking VA conduction as having SVT when said computer detects an arrhythmia exhibiting a 1:1 atrial to ventricular relationship. In one embodiment, the algorithm identifies a patient with AV conduction as having VT if the cycle length of an arrhythmia exhibiting a 1:1 atrial to ventricular relationship is less than the minimum AVW cycle length. In another embodiment, the algorithm identifies a patient with VA conduction as having SVT if the cycle length of an arrhythmia exhibiting a 1:1 atrial to ventricular relationship is less than the minimum VAW cycle length. In yet another embodiment, the algorithm identifies a patient with AV conduction as having SVT if the cycle length of said arrhythmia exhibiting a 1:1 atrial to ventricular relationship is greater than the minimum AVW cycle length but is less than the minimum VAW cycle length. In one embodiment, an operator manually enters information regarding a patient's AV and VA conduction status into said microprocessor. In another embodiment, the minimum AVW and VAW cycle lengths are updated automatically. In yet another embodiment, the update occurs when the patient is at an elevated sympathetic state.

One embodiment of the present invention contemplates a novel capability that detects an earliest arriving electrical signal (i.e., an intracardiac electrogram) that discriminates between SVT and VT. This technique is based on intracardiac electrograms (EGMs) recorded by atrial and ventricular sensing leads that distinguish their temporal relationships following tachycardia recurrence subsequent to a train of simultaneous anti-tachycardia pacing (ATP) bursts in the atria and ventricles.

Another embodiment of the present invention contemplates a method, comprising: a) providing: i) a patient implanted with a device, comprising; 1) an implantable pacemaker element; 2) an implantable defibrillator element connected to said pacemaker element; 3) a plurality of atrial and ventricular pacing leads connected to said pacemaker element, wherein said pacing leads are configured for simultaneous activation and course to the ventricles and atria, wherein said pacemaker is capable of analyzing an electrocardiogram; and 4) an arrhythmia discrimination algorithm; ii) a plurality of sensing leads connected to said pacemaker coursing to the ventricles and atria; iii) a plurality of defibrillation leads connected to said defibrillator coursing to the ventricles; b) detecting ventricular and atrial electrical signals by said sensing leads; c) identifying a cardiac arrhythmia with said device; d) initiating one or more anti-tachycardia pacing bursts by said pacemaker element, wherein said ventricles and atria are simultaneously paced; e) detecting an earliest arriving electrical signal following termination of said anti-tachycardia pacing burst. In one embodiment, the algorithm determines the minimum AVW cycle length of an earliest arriving electrical signal in the ventricles following pacing of the atria, and the minimum VAW cycle length of an earliest arriving electrical signal in the atria following pacing of the ventricles. In another embodiment, the algorithm identifies a patient lacking AV conduction as having VT when said computer detects an arrhythmia exhibiting a 1:1 atrial to ventricular relationship. In yet another embodiment, the said algorithm identifies a patient lacking VA conduction as having SVT when said computer detects an arrhythmia exhibiting a 1:1 atrial to ventricular relationship. In one embodiment, the algorithm identifies a patient with AV conduction as having VT if the cycle length of an arrhythmia exhibiting a 1:1 atrial to ventricular relationship is less than the minimum AVW cycle length. In another embodiment, the algorithm identifies a patient with VA conduction as having SVT if the cycle length of an arrhythmia exhibiting a 1:1 atrial to ventricular relationship is less than the minimum VAW cycle length. In yet another embodiment, the algorithm identifies a patient with AV conduction as having SVT if the cycle length of said arrhythmia exhibiting a 1:1 atrial to ventricular relationship is greater than the minimum AVW cycle length but is less than the minimum VAW cycle length. In one embodiment, an operator manually enters information regarding a patient's AV and VA conduction status into said microprocessor. In another embodiment, the minimum AVW and VAW cycle lengths are updated automatically. In yet another embodiment, the update occurs when the patient is at an elevated sympathetic state.

Another embodiment of the present invention contemplates a method, comprising: a) providing; i) a patient; ii) an electrocardiogram array; iii) a plurality of intracardiac quadripole catheters, wherein said catheters are configured for simultaneous atrial and ventricular pacing; iv) a computer configured to receive electrical signals from said catheters; and v) an arrhythmia discrimination algorithm; b) placing said array on the skin surface of said patient; c) inserting said catheters into said patient; d) simultaneously pacing said atria and ventricle; e) detecting with said computer an earliest arriving electrical signal. In one embodiment, the algorithm determines the minimum AVW cycle length of an earliest arriving electrical signal in the ventricles following pacing of the atria, and the minimum VAW cycle length of an earliest arriving electrical signal in the atria following pacing of the ventricles. In another embodiment, the algorithm identifies a patient lacking AV conduction as having VT when said computer detects an arrhythmia exhibiting a 1:1 atrial to ventricular relationship. In yet another embodiment, the said algorithm identifies a patient lacking VA conduction as having SVT when said computer detects an arrhythmia exhibiting a 1:1 atrial to ventricular relationship. In one embodiment, the algorithm identifies a patient with AV conduction as having VT if the cycle length of an arrhythmia exhibiting a 1:1 atrial to ventricular relationship is less than the minimum AVW cycle length. In another embodiment, the algorithm identifies a patient with VA conduction as having SVT if the cycle length of an arrhythmia exhibiting a 1:1 atrial to ventricular relationship is less than the minimum VAW cycle length. In yet another embodiment, the algorithm identifies a patient with AV conduction as having SVT if the cycle length of said arrhythmia exhibiting a 1:1 atrial to ventricular relationship is greater than the minimum AVW cycle length but is less than the minimum VAW cycle length. In one embodiment, an operator manually enters information regarding a patient's AV and VA conduction status into said microprocessor. In another embodiment, the minimum AVW and VAW cycle lengths are updated automatically. In yet another embodiment, the update occurs when the patient is at an elevated sympathetic state.

In a further embodiment the present invention contemplates a method to detect the origin of a cardiac arrhythmia, comprising: a) providing; i) a patient exhibiting cardiac arrhythmia; ii) an array comprising sensing leads; iii) a computer connected to said array; iv) pacing leads connected to said computer; and v) an arrhythmia discrimination algorithm; b) simultaneously pacing the atria and ventricles with said pacing leads of said patient under conditions such that said patient atrial and ventricular activity is synchronized; and c) sensing with said sensing leads said atrial and ventricular electrical activity after said pacing under conditions such that the earliest arriving electrical activity is detected. In one embodiment, the algorithm determines the minimum AVW cycle length of an earliest arriving electrical signal in the ventricles following pacing of the atria, and the minimum VAW cycle length of an earliest arriving electrical signal in the atria following pacing of the ventricles. In another embodiment, the algorithm identifies a patient lacking AV conduction as having VT when said computer detects an arrhythmia exhibiting a 1:1 atrial to ventricular relationship. In yet another embodiment, the said algorithm identifies a patient lacking VA conduction as having SVT when said computer detects an arrhythmia exhibiting a 1:1 atrial to ventricular relationship. In one embodiment, the algorithm identifies a patient with AV conduction as having VT if the cycle length of an arrhythmia exhibiting a 1:1 atrial to ventricular relationship is less than the minimum AVW cycle length. In another embodiment, the algorithm identifies a patient with VA conduction as having SVT if the cycle length of an arrhythmia exhibiting a 1:1 atrial to ventricular relationship is less than the minimum VAW cycle length. In yet another embodiment, the algorithm identifies a patient with AV conduction as having SVT if the cycle length of said arrhythmia exhibiting a 1:1 atrial to ventricular relationship is greater than the minimum AVW cycle length but is less than the minimum VAW cycle length. In one embodiment, an operator manually enters information regarding a patient's AV and VA conduction status into said microprocessor. In another embodiment, the minimum AVW and VAW cycle lengths are updated automatically. In yet another embodiment, the update occurs when the patient is at an elevated sympathetic state.

Another embodiment of the present invention contemplates a method, comprising: a) providing: i) a patient implanted with a device, comprising; 1) an implantable pacemaker element; 2) a plurality of atrial and ventricular pacing leads connected to said pacemaker element, wherein said pacing leads are configured for simultaneous activation and coursing to the ventricles and atria; and 3) an arrhythmia discrimination algorithm; ii) a plurality of sensing leads connected to said pacemaker coursing to the ventricles and atria; b) initiating one or more pacing bursts by said pacemaker element, wherein said ventricles and atria are simultaneously paced; and c) detecting an earliest arriving electrical signal following termination of said pacing bursts. In one embodiment, prior to step b), a cardiac arrhythmia is detected in said patient. In one embodiment, the algorithm determines the minimum AVW cycle length of an earliest arriving electrical signal in the ventricles following pacing of the atria, and the minimum VAW cycle length of an earliest arriving electrical signal in the atria following pacing of the ventricles. In another embodiment, the algorithm identifies a patient lacking AV conduction as having VT when said computer detects an arrhythmia exhibiting a 1:1 atrial to ventricular relationship. In yet another embodiment, the said algorithm identifies a patient lacking VA conduction as having SVT when said computer detects an arrhythmia exhibiting a 1:1 atrial to ventricular relationship. In one embodiment, the algorithm identifies a patient with AV conduction as having VT if the cycle length of an arrhythmia exhibiting a 1:1 atrial to ventricular relationship is less than the minimum AVW cycle length. In another embodiment, the algorithm identifies a patient with VA conduction as having SVT if the cycle length of an arrhythmia exhibiting a 1:1 atrial to ventricular relationship is less than the minimum VAW cycle length. In yet another embodiment, the algorithm identifies a patient with AV conduction as having SVT if the cycle length of said arrhythmia exhibiting a 1:1 atrial to ventricular relationship is greater than the minimum AVW cycle length but is less than the minimum VAW cycle length. In one embodiment, an operator manually enters information regarding a patient's AV and VA conduction status into said microprocessor. In another embodiment, the minimum AVW and VAW cycle lengths are updated automatically. In yet another embodiment, the update occurs when the patient is at an elevated sympathetic state.

Another embodiment of the present invention contemplates a method, comprising: a) providing; i) a patient; ii) an electrocardiogram array; iii) a plurality of intracardiac quadripole catheters, wherein said catheters are configured for simultaneous atrial and ventricular pacing; iv) a computer configured to receive electrical signals from said catheters; and v) an arrhythmia discrimination algorithm; b) placing said array on the skin surface of said patient; c) inserting said catheters into said patient; d) simultaneously pacing said atria and ventricles; and e) detecting with said computer an earliest arriving electrical signal. In one embodiment, the algorithm determines the minimum AVW cycle length of an earliest arriving electrical signal in the ventricles following pacing of the atria, and the minimum VAW cycle length of an earliest arriving electrical signal in the atria following pacing of the ventricles. In another embodiment, the algorithm identifies a patient lacking AV conduction as having VT when said computer detects an arrhythmia exhibiting a 1:1 atrial to ventricular relationship. In yet another embodiment, the said algorithm identifies a patient lacking VA conduction as having SVT when said computer detects an arrhythmia exhibiting a 1:1 atrial to ventricular relationship. In one embodiment, the algorithm identifies a patient with AV conduction as having VT if the cycle length of an arrhythmia exhibiting a 1:1 atrial to ventricular relationship is less than the minimum AVW cycle length. In another embodiment, the algorithm identifies a patient with VA conduction as having SVT if the cycle length of an arrhythmia exhibiting a 1:1 atrial to ventricular relationship is less than the minimum VAW cycle length. In yet another embodiment, the algorithm identifies a patient with AV conduction as having SVT if the cycle length of said arrhythmia exhibiting a 1:1 atrial to ventricular relationship is greater than the minimum AVW cycle length but is less than the minimum VAW cycle length. In one embodiment, an operator manually enters information regarding a patient's AV and VA conduction status into said microprocessor. In another embodiment, the minimum AVW and VAW cycle lengths are updated automatically. In yet another embodiment, the update occurs when the patient is at an elevated sympathetic state.

Yet another embodiment of the present invention contemplates a method to detect the origin of a cardiac arrhythmia, comprising: a) providing; i) a patient exhibiting cardiac arrhythmia; ii) a system comprising a plurality of pacing leads and a plurality of sensing leads; and iii) an arrhythmia discrimination algorithm; b) simultaneously pacing the atria and ventricles of said patient; and c) sensing with said sensing leads said atrial and ventricular electrical activity after said pacing under conditions such that the earliest arriving electrical signal is detected. In one embodiment, the algorithm determines the minimum AVW cycle length of an earliest arriving electrical signal in the ventricles following pacing of the atria, and the minimum VAW cycle length of an earliest arriving electrical signal in the atria following pacing of the ventricles. In another embodiment, the algorithm identifies a patient lacking AV conduction as having ventricular VT when said computer detects an arrhythmia exhibiting a 1:1 atrial to ventricular relationship. In yet another embodiment, the said algorithm identifies a patient lacking VA conduction as having SVT when said computer detects an arrhythmia exhibiting a 1:1 atrial to ventricular relationship. In one embodiment, the algorithm identifies a patient with AV conduction as having VT if the cycle length of an arrhythmia exhibiting a 1:1 atrial to ventricular relationship is less than the minimum AVW cycle length. In another embodiment, the algorithm identifies a patient with VA conduction as having SVT if the cycle length of an arrhythmia exhibiting a 1:1 atrial to ventricular relationship is less than the minimum VAW cycle length. In yet another embodiment, the algorithm identifies a patient with AV conduction as having SVT if the cycle length of said arrhythmia exhibiting a 1:1 atrial to ventricular relationship is greater than the minimum AVW cycle length but is less than the minimum VAW cycle length. In one embodiment, an operator manually enters information regarding a patient's AV and VA conduction status into said microprocessor. In another embodiment, the minimum AVW and VAW cycle lengths are updated automatically. In yet another embodiment, the update occurs when the patient is at an elevated sympathetic state.

DEFINITIONS

As used herein, the term "cardiovascular disease" refers to any disease which affects the cardiovascular system including, but not limited to, nerve conduction disorders, thrombophilia, atherosclerosis, angina pectoris, hypertension, arteriosclerosis, myocardial infarction, congestive heart failure, cardiomyopathy, hypertension, arterial and venous stenosis, and arrhythmias.

"Symptoms of cardiovascular disease" as used herein refers to any clinical manifestation of a disease state associated with the heart and the central or peripheral arterial and venous vasculature. For example, said clinical manifestations include, but are not limited to pain, weakness, high blood pressure, elevated plasma cholesterol, elevated plasma fatty acids, tachycardia, bradycardia, abnormal electrocardiogram, external or internal bleeding, headache, dizziness, nausea and vomiting. Thus, a patient suffering from, or exhibiting symptoms of, cardiovascular disease may detect certain symptoms (i.e., pain), while other symptoms may not be noticeable to the patient, but are detectable by a health care provider (i.e., elevated blood pressure).

As used herein, the term "patient" refers to a human or non-human organism that is either symptomatic or asymptomatic for cardiovascular disease. Preferably, a human patient is under the supervision of a physician or hospitalized.

As used herein the phrase, "patients at risk for cardiovascular disease" refer to patients who have an increased probability, as compared to the general population, of developing some form of cardiovascular disease in their lifetime. Patients at risk for cardiovascular disease generally have one or more risk factors for cardiovascular disease. Risk factors for cardiovascular disease include, but are not limited to, a history of smoking, a sedentary lifestyle, a family history of cardiovascular disease, lipid metabolic disorders, diabetes mellitus and obesity.

As used herein, the term "pathophysiological" refers to any condition in an individual or an organ that represents a significant deviation from established homeostatic norms. A pathophysiological alteration is not a structural defect.

As used herein, the term "elevated sympathetic state" refers to conditions associated with higher sinus heart rate. Such conditions may correlate with an individual's level of activity or their physical or emotional status.

As used herein, the term "intrinsic heart rate" refers to the number of contractions of the heart (heart beats) in a given time period, often expressed as the number of heart beats per minute. The normal resting heart rate for an adult varies from 60 to 100 beats per minute. Numerous factors, such as exercise and stress, may result in an elevated heart rate as high as 200 beats per minute.

As used herein, the term "electrocardiogram" (EKG or ECG) refers to any display of information reflecting changes in heart tissue membrane potentials in relationship to heart beat. The electrocardiogram comprises "electrogram activity" (EGM) that refers to any electrical signal detected by any sensing lead.

As used herein, the term "electrocardiogram array" refers to any arrangement of skin surface electrodes wherein the integration of the collected data results in the generation of an electrocardiogram.

As used herein, the term "skin surface" refers to the outer epithelial layer of a patient.

As used herein, the term "catheter" refers to any device that is used for the insertion and placement of electrocardiogram sensing leads into the intracardial space. Placement of such a device may be inserted into, but is not limited to, the femoral vein, then coursing through the vena cava and finally into the right atria and/or ventricle of the patient's heart.

As used herein, the term "coursing" refers to a path taken through a patient's body by an implanted catheter or electrical leads that may be, but are not limited to, those connected to an implanted ICD, pacemaker or combination thereof.

As used herein, the term "computer" refers to any device capable of receiving, storing and calculating data in an electronic format.

As used herein, the term "microprocessor" refers to a programmable digital electronic component that incorporates the functions of a central processing unit on a single semi-conducting integrated circuit.

As used herein, the term "sinus rhythm" refers to a normal heartbeat as quantified by the proper relationships between the P-Q-R-S-T electrocardiogram segments.

As used herein, the term "arrhythmia" refers to an abnormal heart beat as quantified by improper relationships between the P-Q-R-S-T electrocardiogram segments. Such arrhythmias may occur during, but are not limited to, ventricular arrhythmia, supraventricular tachycardia (SVT), ventricular fibrillation, atria fibrillation, and bradycardia.

As used herein, the term "atrial EGM" refers to electrogram activity from electrodes whose sensory input is limited to membrane potential changes of the atria. Specifically, these data are collected from, but is not limited to, a high right atrial intracardial electrode placed by catheterization.

As used herein, the term "ventricular EGM" refers to electrogram activity from electrodes whose sensory input is limited to membrane potential changes of the ventricles. Specifically, these data are collected from, but is not limited to, a right ventricular apex intracardiac electrode placed by catheterization.

As used herein, the term "depolarization" refers to the change in membrane potential that reflects the conduction of an "action potential" which initiates and coordinates the relative contractions of the left/right atria with the left/right ventricles. Specifically, these changes in membrane potential are generated by, but not limited to, the pacemaker cells residing in the right atrium.

As used herein, the term "direction of depolarization" refers to the movement of the electric potential across the heart surface. Specifically, an "antegrade" direction refers to a spreading of the depolarization from the atria onto the ventricles and subsequent proper coordination of the heartbeat. On the other hand, a "retrograde" direction refers to a spreading of the depolarization away from the ventricles to the top of the atria and as a result of ventricular arrhythmias.

As used herein, the term "data readout device" refers to any instrument that may be connected to a computer that receives and displays the results of computer calculations. These instruments may be, but are not limited to, an electronic monitor, a hardcopy printout, and an audible signal generated by a computer sound generation program.

As used herein, the term "cardiac defibrillator" refers to any device that generates an "electroshock" that is expected to restore normal sinus rhythm in a patient experiencing an abnormal ECG. These devices may include, but are not limited to, defibrillators that are safe and effective when surgically implanted in a patient and auto-activate upon sensing an abnormal ECG. Specifically, these devices may be, but are not limited to, dual-chamber cardioverter-defibrillators. A "dual-chamber" design is preferred over other cardioverter-defibrillators because they provide an ability to simultaneously control the rate of ventricular and atrial contraction and sense their relative electrical activity.

As used herein, the term "inappropriate electroshock" refers to any electroshock generated by a cardiac defibrillator that is delivered by misinterpretation of an ECG. This ECG misinterpretation may occur during, but is not limited to, sinus tachycardia or other supraventricular tachycardias (SVT).

As used herein, the term "pace" or "pacing" refers to an artificial electrical stimulation of a heart chamber that supersedes the function of physiological pacemaker cells. The artificial electrical stimulation may, but is not limited to, be generated by an electrode within an intracardiac catheter or an ICD.

As used herein, the term "atria" refers to the upper principal cavity of the heart auricle (i.e., the sinus venosus) and is situated posteriorly to the smaller cavity of the auricle, the appendix auricula. The human heart comprises two atria, one on the left side of the heart and a second on the right side of the heart. Consequently, the term "atrial" references any matter of, or concerning, either one or both atria.

As used herein, the term "ventricle" refers to the lower, and largest, compartment of the heart. The human heart comprises two ventricles, one on the left side of the heart and a second on the right side of the heart. Consequently, the term "ventricular" references any matter of, or concerning, either one or both ventricles.

As used herein, the term "atrioventricular node" (AV node) refers to an area of specialized tissue between the atria and the ventricles of the heart, which conducts the normal electrical impulse from the atria to the ventricles. The AV node is also known as the Aschoff-Tawara node.

As used herein, the term "1:1 atrial to ventricular relationship" or "1:1 AV relationship" refers to an arrhythmia wherein electrical signals detected from the atria and ventricles exhibit a 1:1 ratio. Electrical signals are conducted from one cardiac chamber to another at a "1:1 ratio" when each electrical impulse in the atria results in a corresponding electrical impulse in the ventricles, or vice versa. Specifically, an arrhythmia wherein the electrical signal exhibits "1:1 ventricular to atrial conduction" or "1:1 VA conduction" represents a potentially life-threatening ventricular tachycardia. Similarly, an arrhythmia wherein the electrical signal exhibits "1:1 atrial to ventricular conduction" or "1:1 AV conduction" represents a non life-threatening supraventricular tachycardia.

As used herein, the term "atrioventricular" refers to an electrical signal conducted from the atria to the ventricles.

As used herein, the term "AV conduction" refers to an electrical signal conducted from the atria to the ventricles. AV conduction is usually present in most patients, but not in all. Conditions where it may be absent include but are not limited to congenital heart diseases, infectious or infiltrative heart disease, or cases where the AV conduction was permanently interrupted as a result of an ablation procedure. Absence of AV conduction is compatible with life if the patient has an intrinsic escape rhythm in the lower chambers of the heart or if the patient is supported by artificial pacing of the lower chambers of the heart such as from a pacemaker or a defibrillator. The patient's baseline status of AV conduction is established prior to the time of the implantation of a cardiac device such as a pacemaker or ICD, by analyzing a routine ECG or cardiac monitor strip, for example.

As used herein, the term "ventriculoatrial" refers to an electrical signal conducted from the ventricles to the atria.

As used herein, the term "VA conduction" refers to an electrical signal conducted from the ventricles. Unlike the case with AV conduction, the absence of VA conduction is very common in normal human beings. It is estimated that about 40% to 50% of all normal individuals lack the ability to conduct electrical impulses from the ventricles to the atria. The patient's baseline status of VA conduction is established prior to or at the time of the implantation of a cardiac device such as a pacemaker or ICD, by pacing their ventricles and looking for conduction of the electrical impulses to the atria.

As used herein, the term "AVW cycle length" or "AV Wenckebach cycle length" or "Atrioventricular Wenckebach cycle length" refers to the maximum rate at which an electrical signal can be detected in the ventricles following electrical pacing of the atria in a 1:1 fashion. The "AVW cycle length" of an individual may be determined by pacing the atria for one or more beats with increasingly shorter coupling intervals until a corresponding event in the ventricles is no longer sensed.

As used herein, the term "Minimum AVW cycle length" refers to an AVW cycle length that is updated every time a smaller value for the AVW cycle length is achieved.

As used herein, the term "VAW cycle length" or "VA Wenckebach cycle length" or "Ventriculoatrial Wenckebach cycle length" refers to the maximum rate at which an electrical signal can be detected in the atria following electrical pacing of the ventricles in a 1:1 fashion. The "VAW cycle length" of an individual may be determined by pacing the ventricles for one or more beats with increasingly shorter coupling intervals until a corresponding event in the atria is no longer sensed.

As used herein, the term "Minimum VAW cycle length" refers to a VAW cycle length that is updated every time a smaller value for the VAW cycle length is achieved.

As used herein, the term "blanking period" refers to any cessation of electrogram (EGM) activity from either an atrial or ventricular chamber. A blanking period may be triggered by, but not limited to, an anti-tachycardia pacing (ATP) burst. Specifically, a blanking period is the shortest period of time, in milliseconds, as measured from the last ATP pacing burst that would include the first captured electrogram (EGM) activity from either the atrial and ventricular channels that varies as function of tachycardial cycle length. An exemplary calculation of a blanking period might be: $(100+TCL)/2$ where TCL is the tachycardia cycle length. The expected duration of a blanking period in a human patient is approximately, but not limited to, 100 to 500 msec.

As used herein, the term "anti-tachycardia pacing burst" refers to any train of electrical impulses generated from, for example, an ICD or an external signal generator, during an episode of either SVT or ventricular arrhythmia that provides pacing stimulus to either the atria, ventricles or both. Preferably, the generated signals are of a square-wave morphology. A "simultaneous anti-tachycardia pacing burst" refers to any pacing signals provided to both the atria and ventricle within any 0 to 40 msec timeframe. Generally, multiple anti-tachycardia pacing bursts are delivered; wherein each burst has an approximate length of twelve heartbeats.

As used herein, the term "storage memory" refers to any electronic means that is capable of retaining digitized information or computer software programs. The digitized information may be binary or complex formulas or equations capable of receiving, and processing, input from atrial or ventricular sensing leads.

As used herein, the term "defibrillation leads" refer to any electrical conductive material placed on, or within, a heart chamber that, when activated, is capable of converting an abnormal heart rhythm into normal sinus rhythm.

As used herein, the term "sensing leads" refer to any electrical conductive material placed on, or within, a heart chamber that transmits electrical activity.

As used herein, the term "pacing leads" refer to any electrical conductive material placed on, or within, a heart chamber that, when activated, provides an electrical stimulus to control cardiac muscle contractility.

As used herein, the phrase "the capability of detecting an earliest arriving electrical signal" (or analogous phrases) refers to any electronic configuration that is capable of discriminating the arrival time between at least two electrical signals having a sensitivity of ranging between 0 to 40 msec. While not intending to limit any embodiment of the present invention, the sensing of atrial EGM or ventricular EGM may be performed with, or without, calculations based on any formula or equations. For example, EGMs may be filtered by the pacemaker and connected to a timing device. The output may be, but is not limited to, a binary format. At a minimum, the detection capability answers two questions; i) Did the tachycardia terminate? (yes/no), and if it did not terminate, ii) Was the ventricular EGM prior to the atrial EGM? (yes/no).

As used herein, the term "earliest arriving electrogram activity" refers to the first electrical signal detected following a specific timeline marker (i.e., an anti-tachycardia pacing burst).

As used herein, the term "simultaneously arriving electrogram activity" refers to at least two electrical signals detected within a 50 to 60 msec timeframe.

As used herein, the term "system" refers to any integrated single device, or multiple devices connected together, that function in a coordinated manner to produce a desired result. One example illustrated herein, describes a system that detects an earliest arriving electrical signal comprising integrated single device such as an ICD comprising a pacemaker. Another example illustrated herein, describes a system that detects and earliest arriving electrical signal comprising multiple devices connected together such as an electrocardiogram array, a generator (i.e., for example, pulse or signal) and a computer.

As used herein, the term "algorithm" refers to a precise list of precise steps, and/or a finite list of well-defined instructions, for accomplishing some task that, given an initial state, will terminate in a defined end-state.

As used herein, the term "discrimination algorithm" refers to an algorithm capable of identifying the source of an arrhythmia exhibiting 1:1 AV conduction as either VT or SVT based on an individual's baseline VA and/or AV conduction status as well as their AVW cycle length and/or VAW cycle length.

As used herein, the term "endocardial" refers to the innermost layer of tissue that lines the chambers of the heart. During ventricular contraction, the wave of depolarization moves from the endocardial surface to the epicardial surface. Consequently, the endocardial surface represents a potential site for cardiac pacing.

As used herein, the term "epicardial" refers to the outer layer of tissue that functions as a protective layer for the heart. During ventricular contraction, the wave of depolarization moves to the epicardial surface from the endocardial surface. Consequently, the epicardial surface represents a potential site for cardiac pacing.

As used herein, the term "decrement" refers to the act or process of decreasing, such as a negative increment or the amount lost by reduction.

BRIEF DESCRIPTION OF THE DRAWINGS

FIG. 4A shows VT persistence in a human patient following 400 msec anti-tachycardia pacing bursts. (blanking period from last ATP stimulation to dashed line)

DETAILED DESCRIPTION OF THE INVENTION

Figure 1:
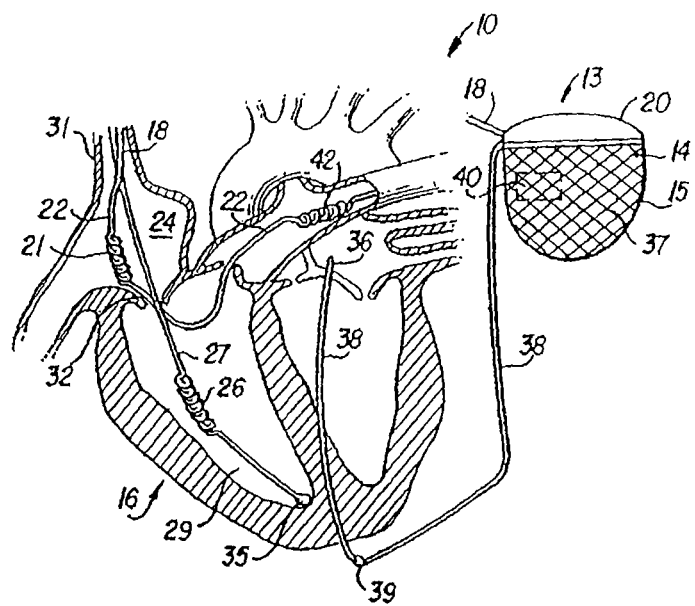
FIG. 1 depicts a cutaway drawing of an exemplary human heart showing the configuration of one embodiment of dual chamber implantable cardiac pacer/defibrillator

This invention relates to the identification and detection of abnormal heart rhythm occurring in either the supraventricular or ventricular cardiac regions. Specifically, this invention relates to a novel method of analysis to discriminate between SVT and ventricular arrhythmia. More specifically, this invention relates to an ICD device controlled by a novel method of analysis to discriminate between SVT and ventricular arrhythmia.

The present invention contemplates a novel capability that detects an electrical signal conducted through the atrioventricular (AV) node in both directions to distinguish the origin of an arrhythmia with a 1:1 atrial to ventricular relationship as SVT or VT. This technique is based on intracardiac electrograms (EGMs) recorded by atrial and ventricular sensing leads that determine the rate of cardiac AV and VA conduction both at baseline and under various conditions over time to discriminate between VT and SVT. Information regarding the characteristics of AV and VA conduction may be manually provided to the ICD through a programmer and can be regularly updated through on-going, automated, periodic assessment subsequent to a train of pacing bursts in the atria and ventricles.

This invention relates to the real-time identification and detection of abnormal heart rhythm occurring in either the supraventricular or ventricular cardiac regions. Specifically, this invention relates to a novel method of analysis to discriminate between SVT and ventricular arrhythmia. More specifically, this invention relates to an ICD device controlled by a novel method of analysis that discriminates between SVT and ventricular arrhythmia.

The clinical manifestations of ventricular arrhythmias range from a complete absence of symptoms to sudden death. Although the understanding of the pathophysiology and natural history of these arrhythmias has advanced significantly over the past decade, large gaps in knowledge remain, especially in patients with heart failure not due to coronary artery disease. Many symptomatic ventricular arrhythmias, however, are now curable using catheters that deliver radio-frequency energy (i.e., ablation lesioning). It is now clear that the primary treatment for patients at high risk for life-threatening ventricular arrhythmias is the ICD.

Determination of atrial tissue depolarization directionality has met with little success. Various time and frequency domain criteria have been mathematically applied to the bipolar atrial electrogram, which achieve successful discrimination of atrial depolarization directionality in less than 80% of patients. Timmis et al., Discrimination Of Antegrade From Retrograde Atrial Electrograms For Physiologic Pacing, PACE 11:130 140 (1988); Wainwright et al., Ideal Atrial Lead Positioning To Detect Retrograde Atrial Depolarization By Digitization And Slope Analysis Of The Atrial Electrogram, PACE 7:1152 1158 (1984). Similarly, the use of amplitude and slew rate criteria resulted in successful discrimination of antegrade versus retrograde atrial depolarization in 81% of patients (McAlister et al., Atrial Electrogram Analysis: Antegrade Versus Retrograde, PACE 11:1703 1707 (1988)). This in contrast to an initial promising study that could not be reproduced. Pannizo et al., Discrimination Of Antegrade And Retrograde Atrial Depolarization By Electrogram Analysis, Am Heart J. 112:780 786 (1986).

In an attempt to solve this problem, those skilled in the art have attempted using various mathematical algorithms to utilize the quantitative embodiments of the ECG with variable success. Specifically, the morphology of a shocking electrogram may be compared to a sinus beat template. Gold et al., A New Defibrillator Discrimination Algorithm Utilizing Electrogram Morphology Analysis, Pacing Clin Electrophysiol. 1999; 22:179 182 (1999) Additionally, stability criteria may be employed to distinguish between atrial fibrillation and ventricular arrhythmia. Barold et al., Prospective Evaluation Of New And Old Criteria To Discriminate Between Supraventricular And Ventricular Tachycardia In Implantable Defibrillators, Pacing Clin Electrophysiol., 21:1347 1355 (1998); and Schaumann et al., Enhanced Detection Criteria In Implantable Cardioverter-Defibrillator To Avoid Inappropriate Therapy, Am J Cardiol., 78:42 50 (1996). In comparison, discrimination between sinus tachycardia and ventricular arrhythmia may be determined by the employment of sudden onset criteria. These approaches have reduced the rate of inappropriate electroshocks, but continue to remain at approximately 11%. Schaumann et al. (supra).

The advent of atrioventricular conduction metrics improved the discrimination between ventricular arrhythmia and 1:1 SVT where 80% specificity was coupled with 100% sensitivity when ventriculoatrial times were between 80 and 234 ms. Thompson et al., Ventriculoatrial Conduction Metrics For Classification Of Ventricular Tachycardia With 1:1 Retrograde Conduction In Dual-Chamber Sensing Implantable Cardioverter Defibrillators, J Electrocardiol., 31:152 156 (1988) Beyond these boundaries, both the sensitivity and specificity were 100%. Similarly, correlational waveform analysis was able to discriminate between antegrade and retrograde atrial activation, in the absence of ventricular arrhythmia, during ventricular pacing when patient-specific thresholds were adopted and the sampling rate of the signal was set at 1,000 Hz or greater. Throne et al., Discrimination Of Retrograde From Antegrade Atrial Activation Using Intracardiac Electrogram Waveform Analysis, Pacing Clin Electrophysiol., 12:1622 1630 (1989)

The impact of heart rate and sympathetic tone on the shape of intracardiac ECG waveforms has been assessed. In 36 out of 39 patients, increased heart rates resulting from; i) atrial pacing, ii) epinephrine infusion, and iii) isoproterenol infusion did not significantly alter ECG waveform configuration as assessed by correlation waveform analysis. Finelli et al., Effects Of Increased Heart Rate And Sympathetic Tone On Intraventricular Electrogram Morphology, Am J Cardiol. 68:1321 1328 (1991) In patients with permanent pacemakers, exercise results in a 38% decrease in atrial ECG amplitude without any other morphologic changes. Ross et al., The Effect Of Exercise On The Atrial Electrogram Voltage In Young Patients, PACE, 14:2092 2097 (1991) The correlation coefficients (.rho.) generated by correlation waveform analysis is independent of amplitudes and units and should not be adversely impacted by heart rate, sympathetic tone or exercise. Woodroofe M., Probability With Applications, McGraw-Hill, New York. pp. 229 (1975) It is possible, however, that changes in atrial morphology may occur over time and changing patient posture. A critical analysis of these variables would require the use of chronic sensing leads.

In U.S. Pat. No. 6,076,014 (herein incorporated by reference), an implantable dual chamber defibrillator capable of dual chamber pacing is disclosed. This defibrillator is revealed as capable of providing continuous atrial pacing or pacing of ventricular chambers as a response to a detected arrhythmia. Specifically, the '014 disclosure evaluates sensed ECG data by a fuzzy logic paradigm that is acknowledged to be imprecise. The fuzzy logic assessment in the '014 patent includes input regarding: i) atrial rates, ii) ventricular rates, iii) ECG morphology, iv) the historical trends of ECG data, and v) accelerometer data (i.e., real-time measurement of patient movements).

The present application provides a novel method and device when compared to the '014 patent as well as being simple, specific, accurate. Although it is not necessary to understand the mechanism of an invention, it is believed the disclosed capability of detecting an earliest arriving electrical signal reliably discriminates between ventricular arrhythmia and SVT and objectively provides a defibrillation decision only for a condition of ventricular arrhythmia. Specifically, this capability relies on the relative arrival times of electrical activity from either the ventricles or the atria, after synchronization by simultaneous pacing. The '014 makes no mention of using anti-tachycardia pacing in combination with a blanking period to assess which heart chamber resumes activity first. Instead, the '014 patent relies on IF-THEN statements that requires information on patient activity and the relative ventricular and atrial rates.

1) Heart Function

The operation of the heart is regulated by electrical signals produced by the heart's sino-atrial (SA) node. Each signal produced by the SA node spreads across the atria and ventricles of the heart, depolarizing the muscle fibers as it spreads. Atrial and ventricular contractions occur as the signal passes. After contracting, the myocardial cells repolarize during a short period of time, returning to their resting state. Once repolarized, the muscle cells are ready to be depolarized again by a signal from the SA node.

At rest, the normal adult SA node produces a signal approximately 60 to 85 times a minute, causing the heart muscle to contract, and thereby pumping blood to the remainder of the body. This constitutes the repetitive, cyclic behavior of the heart. Each cycle in the operation of the heart is called a cardiac cycle.

Atrial geometry, atrial anisotropy, and histopathologic changes in the left or right atria can, alone or together, form anatomical obstacles. The obstacles can disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria. Abnormal, irregular heart rhythm called arrhythmia, results. This form of arrhythmia is called atrial fibrillation, which is a very prevalent form of arrhythmia.

To analyze the heart's operation, a variety of techniques have been developed for collecting and interpreting data concerning the electrical activity of the heart. One of the most basic of these approaches is the electrocardiogram (ECG). As an electrical signal spreads across the heart, an ECG repetitively measures the voltages at various electrodes relative to a designated "ground" electrode. The ECG typically plots each lead over an interval of time such that the heart's electrical activity for one or more cardiac cycles is displayed for purposes of monitoring or analysis. The three most common ECG's are known as the "12 lead", the "18 lead," and the vector cardiograph.

A cardiac cycle as measured by the ECG is partitioned into three main elements, which reflect the electrical and mechanical operation of the heart. The portion of a cardiac cycle representing atrial depolarization is referred to as a "P-wave." Depolarization of the ventricular muscle fibers is represented by "Q", "R", and "S" points of a cardiac cycle. Collectively these "QRS" points are called an "R-wave" or a "QRS complex." The portion of a cardiac cycle representing repolarization of the ventricular muscle fibers is known as a "T-wave." It is through the use of an ECG that one is able to determine whether fibrillation is or is not occurring and allows one to manipulate the heart tissue to provide treatment.

2) Pacemakers

A pacemaker maintains the heart rate of a patient between a certain programmable range. For example, in humans that range is typically between 60 to 80 beats per minute (lower rate) and 120 to 160 beats per minute (upper rate). In one embodiment, the present invention contemplates a pacemaker for stimulating the independent conduction zones and reestablishing functional communication between the zones. A pacemaker automatically applies a pacing impulse to the heart of sufficient magnitude to depolarize the tissue. The device is adapted to continue delivering intermittent pacing to the heart in the event that the heart fails to return to its normal behavioral pattern, and has the ability of automatically regaining sensing control over a functional heart, thereby insuring that further pacing is inhibited.

The pacemaker circuit comprises two basic subsystems; a sensing system, which continuously monitors heart activity; and a stimulation system, which upon receiving a signal from the sensing system applies a pacing impulse to the myocardium through an intravascular electrical lead. A first bipolar lead may be coupled to the pulse generator and has an electrode located at its distal end to sense and pace the atrium. Alternatively, the atrial leads may comprise separate sensing and pacing electrodes. A second bipolar lead coupled to the generator is used for sensing and pacing the ventricle. Alternatively, the ventricular leads may comprise separate sensing and pacing electrodes. A circuit is provided for applying impedance measuring current pulses between one of these electrodes and the others.

In one embodiment, an off-the-shelf pacemaker is capable of both atrial and ventricular pacing/sensing. The specific pacemakers preferred for this purpose include a Medtronic Sigma, a Medtronic Kappa (both made by Medtronic, Inc. Minneapolis, Minn.), a Guidant Discovery, a Guidant Meridian (both made by Guidant Inc, Minneapolis, Minn.) or Pacesetter Affinity (Pacesetter, a St. Jude's company, Minneapolis, Minn.) as these have a minimum programmable delay between atrial and ventricular pacing of 10 msec.

a) Sensing Elements of a Pacemaker

In a standard dual chambered pacemaker, the sensing circuits monitor activity both in the atrium and ventricle. If a sensed event occurs in the atrium, this initiates a ventricular paced event if no ventricular activity occurs during the programmed atrio-ventricular delay. If no sensing occurs in the atrium or ventricle, pacing is initiated to maintain the programmed lower rate.

When the pacemaker device is used for the present invention, similar sensing algorithms will be useful in the appropriate pacing of the various intracardiac segments. It is particularly desirable that the pacemaker includes a sensor of a physiologic parameter related to demand for cardiac output, such as an activity sensor, a respiration sensor or an oxygen saturation sensor. Various dual chamber pacing devices have incorporated some form of sensor to provide a physiologic pacing rate. Similar sensing is contemplated for the present invention to maintain a physiologic rate.

b) Pacing Elements

In a standard dual chamber pacemaker, pacing of both atrium and ventricle is possible. In the current invention, pacing of the various elements will take place once requested by the sensing algorithm. The standard burst generator pacemaker employs appropriate technology for the generation of stimulation pulses in the form of individual pulses or pulse trains having an amplitude up to 7 V and a pulse width of up to 1 msec. Most pacemakers have these parameters as a programmable option. The pacing rate is also programmable in most pacemakers and the range is between 35 to 160 beats/min.

Given that the circuitry for pulse generation has become well known to those skilled in the art, no detailed disclosure is included herein. Specific timing, amplitude, duration and the number of pulses is controlled by a microprocessor via data bus under the control of a program stored in memory.

c) Arrhythmia Discrimination Algorithm

When the pacemaker device is used for the present invention, a microprocessor using a discrimination algorithm will incorporate information from the sensing and pacing algorithms, as well as information regarding an individual's AV and/or VA conduction profile(s), to identify the source of an arrhythmia exhibiting 1:1 AV conduction as either VT or SVT. Along with automatic updates of an individual's AV and/or VA conduction profiles at times of elevated sympathetic activity, the discrimination algorithm will determine whether an individual experiencing an arrhythmia with 1:1 AV conduction requires defibrillation.

3) Implantable Cardiac Defibrillators

Implantable cardiac defibrillators (ICDs) have significantly reduced the risk of sudden death following hospital discharge, but arrhythmia risk and associated mortality remains an important problem. Buxton et al., Current Approaches To Evaluation And Management Of Patients With Ventricular Arrhythmias, Med Health R I, 84(2):58 62 (2001) Arrhythmias are known to occur in patients having congestive heart failure, atrial fibrillation, ventricular tachyarrhythmias, and bradyarrhythmias. Atrial fibrillation, in particular, is treatable with rate control anticoagulation or cardioversion followed by maintenance of sinus rhythm. In patients surviving malignant ventricular arrhythmias, however, implanted cardiac defibrillators are especially beneficial. Specifically, in patients with coronary artery disease, decreased ejection fraction, with or without non-sustained VT, defibrillator implantation can improve survival. Lampert et al., Management Of Arrhythmias, Clin Geriatr Med, 16(3): 593 618 (2000)

Identifying the mechanism of an arrhythmia based on intracardiac electrograms has become a challenge in the clinical use of ICDs. Implantable cardiac defibrillators are primarily designed to deliver therapy for life-threatening ventricular arrhythmias but frequently deliver inappropriate shocks during a SVT. Tanaka S., An Overview Of Fifth-Generation Implantable Cardioverter Defibrillator, Ann Thorac Cardiovasc Surg., 4:303 311 (1998); Thompson et al., supra; Gold et al., A New Defibrillator Discrimination Algorithm Utilizing Electrogram Morphology Analysis, Pacing Clin Electrophysiol. 1999; 22:179 182 (1999); Barold et al., Prospective Evaluation Of New And Old Criteria To Discriminate Between Supraventricular And Ventricular Tachycardia In Implantable Defibrillators, Pacing Clin Electrophysiol., 21:1347 1355 (1998); and Schaumann et al., Enhanced Detection Criteria In Implantable Cardioverter-Defibrillator To Avoid Inappropriate Therapy, Am J Cardiol., 78:42 50 (1996)

Patients with dual-chamber implantable cardioverter defibrillators continue to receive inappropriate shocks when their ICD fails to discriminate between VT and SVT. Arrhythmias with atrial to ventricular relationships are often the most challenging to categorize by the ICD since they can represent SVT with 1:1 AV conduction or VT with 1:1 VA conduction. Although it is not necessary to understand the mechanism of an invention, it is believed that determining the properties of cardiac AV and VA conduction in ICD's both at baseline and at various intervals afterwards may provide insight to increasing the performance of the ICD in discrimination between VT and SVT.

It is believed that about 40-50% of patients have no retrograde (VA) cardiac conduction. It is also believed that of all patients with complete heart (AV) block, about 15% retain the ability to conduct electrical impulses from the ventricles to the atria. Knowing the characteristics of AV and VA conduction in any given individual with a dual-chamber ICD, allows the ICD to better categorize a 1:1 tachycardia as VT or SVT. For example, if such an arrhythmia is detected in a patient with known lack of VA conduction, then the arrhythmia is certainly SVT. On the other hand, if a patient has complete AV block, then the arrhythmia represents VT with retrograde conduction.

In one embodiment, the present invention contemplates a new defibrillator that has the capability of incorporating in its discrimination algorithms information about the baseline characteristics of AV and VA conduction of the patient undergoing the ICD implantation. An operator, presumably the implanting physician, can enter information regarding the presence or absence of AV and VA conduction. If present, the maximum rate of AV or VA 1:1 conduction can be determined, representing the AV Wenckebach (AVW) or VA Wenckebach (VAW) cycle lengths, and stored in the ICD for use by the discrimination algorithms. In another embodiment, an operator, presumably the implanting physician, can update information regarding the presence or absence of AV and VA conduction after the device has been implanted in the patient. An external update of the presence or absence of AV and VA conduction could occur, for example, following the operator/physician's determination that a patient's AV and/or VA conduction profile has changed.

It is believed that patients' AV and VA conduction characteristics vary based on their level of activity or their physical and emotional status. Conditions where elevated sympathetic states are present (typically associated with a higher sinus heart rate) may allow AV and/or VA conduction to take place, even when no such condition is present at baseline. Although it is not necessary to understand the mechanism of an invention, it is believed that an ICD with the ability to assess AV and VA conduction over time by pacing the various chambers of the heart may provide insight regarding this problem of temporal AV and/or VA conduction variations. In one embodiment, the present invention contemplates assessing AV conduction by pacing the atria with an ICD in short bursts at incrementally faster rates while assessing the ventricular rate and the time relationship between atrial pacing and ventricular sensed events. It is believed that this may allow the determination of the presence of AV conduction, as well as the level of AVW cycle length in case AV conduction is present. In another embodiment, the present invention contemplates assessing VA conduction by pacing the ventricle with an ICD in short bursts at incrementally faster rates while assessing the atrial rate and the time relationship between ventricular pacing and atrial sensed events. It is believed that this may allow the determination of the presence of VA conduction as well as the level of VAW cycle length in case VA conduction is present. In yet another embodiment, the present invention contemplates performing these tests periodically, for example, around times when the sensed atrial rate is elevated, denoting an elevated sympathetic drive. Although it is not necessary to understand the mechanism of an invention, it is believed that upon detection of a tachyarrhythmia with 1:1 relationship, the atrial and ventricular sensed events, their rates, and/or relative timing to each other may be compared to the information learned from the assessment of AV and/or VA conduction. In one embodiment, the present invention contemplates using AV and/or VA conduction information to identify the origin of the abnormal rhythm as coming from the atria or the ventricles.

a) A Dual Chamber Pacing/Sensing Device

FIG. 1 provides one possible embodiment contemplated by the present invention; for example, an implantable cardiac defibrillator (ICD) 13 attached to pacemaker 14. One of skill in the art will easily recognize that the scope of the present invention is not limited by the device herein described. In fact, many possible engineering designs are compatible with the embodiments described herein. It is not intended, therefore, to limit the present invention to the device depicted in FIG. 1.

The pacemaker/defibrillator is implanted in a surgically formed pocket in the flesh of the patient's chest 10, or other desired location of the body. Signal generator 14 is conventional and incorporates electronic components for performing signal analysis and processing, waveform generation, data storage, control and other functions, power supply 40 (battery or battery pack), which are housed in a metal case (can) 15 compatible with the tissue and fluids of the body (i.e., biocompatible). The device is microprocessor-based with substantial memory, logic and other components to provide the processing, evaluation and other functions necessary to determine, select and deliver appropriate therapy including electrical defibrillation and pulses of different energy levels and timing for ventricular defibrillation, cardioversion, and pacing to the patient's heart 16 in response to ventricular arrhythmia and SVT.

Composite electrical lead 18 which includes separate leads 22 and 27 with distally located electrodes is coupled at the proximal end to signal generator 14 through an electrical connector 20 in the header of case 15. Preferably, case 15 is also employed as an electrode such as electrical ground, for unipolar sensing, pacing or defibrillation. Unlike the defibrillator devices used in previous methods, the signal generator and lead(s) of the present invention may be implemented for atrial and ventricular sensing, pacing and defibrillation. Defibrillating shocks of appropriate energy level may be applied between the case and electrode 21 on lead 22 implanted in the right atrium 24 through the superior vena cava 31, or between the case and electrode 26 on lead 27 implanted through the superior vena cava in the right ventricle 29. Leads 22 and 27 and their associated distal tip electrode 32 (to a separate conductor) and distal tip electrode 35 (also to a separate conductor within the lead), respectively, may be used for both a sensing lead and a pacing lead in conjunction with the circuitry of signal generator 14. One of skill in the art may easily recognize that separate sensing and pacing leads are also compatible with this described system. To that end, electrode 32 is positioned in the right atrium against either the lateral or anterior atrial wall thereof, and electrode 35 is positioned in the right ventricle at the apex thereof.

Active or passive fixation of the electrodes may be used to assure suitable excitation. Tip electrode tip 35 preferably has a standard 4 to 8 millimeter (mm) configuration, and is provided with soft barbs (tines) to stabilize its position in the ventricle. Each of the electrodes, those used for defibrillation and cardioversion, as well as those used for sensing and for pacing, are electrically connected to separate conductors in leads 22 and 27.

If desired, rather than simply using metal case 15 as an electrode, a conductive pouch 37 comprised of a braided multiplicity of carbon fine, individual, predominantly isotropic wires such as described in U.S. Pat. No. 5,143,089 (herein incorporated by reference) is configured to receive, partly enclose and maintain firm electrical contact with the case. This serves to enhance the effectiveness of the anodal electrode of the case and establish a better vector for the electric field produced by the defibrillation shock waveform, and thereby lower the defibrillation threshold. The conductive pouch can be electrically connected directly to an extension lead 38 composed of similar carbon braid of about 7 french diameter which is implanted subcutaneously for connection to an epicardial or pericardial patch electrode (not shown) or as a wire electrode (as shown) through an opening formed by puncture surgery at 39. The conductor for electrode 36 of lead 38 may be implanted subcutaneously to a point 39, and then by puncture surgery through the thoracic cage and the pericardial sac, under a local anesthetic. The lead 38 is run parallel to the sternum, through the puncture, and then through the patient's thoracic cage and into the pericardial sac. It may even be threaded through the thoracic cage, the pericardial space about the left ventricle and atrium, and back along the right atrial appendage, external to the heart. The distal end 36 of lead 38 is preferably placed close to the left atrium of the patient's heart to provide an increase in electric field strength and support the strong vector of the electric field according to the heart chamber to be defibrillated. Selection of the chamber (i.e., atrium or ventricle) that is to undergo defibrillation is made by choosing the appropriate endocardial counter-electrode (21 or 26, respectively) to be energized together with the carbon electrode, if the case 15 or conductive pouch 37 is not used directly as the other electrode.

Fabricating the electrode portion of conductor 38 (from the point of entry 39 into the thoracic cage) of carbon braid provides the desirable features described earlier herein. Proper intracardiac positioning improves the vector for defibrillation through the atrium as well as the ventricle.

Atrial coil electrode 21 is used for bipolar sensing as well as a counter-electrode for defibrillation. Hence, electrode 21 is preferably also composed of a braided carbon fiber material described in the '089 patent, to take advantage of its very low polarization and low defibrillation threshold, to allow the intrinsic rhythm to be detected almost immediately after delivery of a shock for accurate determination of the current status of electrical activity of the atrium. The features of low polarization and accurate sensing are important for detection and evaluation of atrial status since atrial signals have magnitudes of only about 20% to 25% those of ventricular signals because of the smaller atrial mass. The braided carbon fiber structure of electrode 21 is also desirable to provide a large effective electrical surface area (for example, in a range from three to six square centimeters) relative to its considerably smaller geometric area, which provides greater energy efficiency for defibrillation.

As with atrial electrode 21, ventricular electrode 26 of lead 27 is positioned for use as a defibrillation electrode as well as for bipolar sensing in the ventricle. For defibrillation, electrode 26 also cooperates with the metal case 15, pouch electrode 37, or pericardial electrode 36, whichever of these latter electrodes is used in the defibrillator implementation. Again, a braided conductive structure for electrode 26 provides it with an effective surface area considerably larger than its actual exposed surface area. As an alternative, the electrode may be composed of fine metallic filaments and fibers of platinum iridium alloy, braided together to offer similarly desirable electrode characteristics.

Thus, the tip electrodes of leads 22 and 27 are used for sensing and pacing of the respective atrial and ventricular chambers as in a conventional pacemaker, with dual-chamber pacing, dual-chamber sensing, and both triggered and inhibited response. Further, the defibrillator 13 uses a transvenous electrode for ventricular defibrillation and stimulation and an atrial bipolar lead for sensing and atrial defibrillation, so that atrial defibrillation is performed with one of the same electrodes used for atrial stimulation and sensing.

Rather than terminating at distal tip electrode 32, the latter electrode may be positioned at mid-lead of the atrial transvenous lead 22 which extends and is threaded through right atrium, ventricle, pulmonary valve, and into the left pulmonary artery, with a coil counter-electrode 42 connected to a separate conductor of the lead. With this alternative embodiment, a defibrillating waveform can be applied between electrode 42 and atrial defibrillation electrode 21 upon detection of atrial fibrillation. In that configuration, electrode 42 would replace signal generator case 15, conductive pouch 37, or lead portion 36 as the selected electrode, and enables a strong vector for the electric field through right and left atrium. Rather than placement in the left pulmonary artery, electrode 42 may be positioned in the distal coronary sinus for defibrillation of the atrium in conjunction with electrode 21.

Defibrillation of the atrium and ventricle is achieved by application of defibrillation waveforms of suitable shape and energy content between appropriate electrodes, such as electrode 36 and electrode 21 for atrial fibrillation, or between electrode 42 and electrode 21 for atrial fibrillation; or between electrode 36 and electrode 26 for ventricular fibrillation, in which atrial electrode 21 can be used additionally as either anode or cathode. The case 15 can serve as the anode for delivery of the shock as well, and can provide ground reference potential for unipolar sensing and pacing, in both chambers.

b) Arrhythmia Discrimination Algorithm

When the defibrillator device is used for the present invention, a microprocessor using a discrimination algorithm will incorporate information from the sensing and pacing algorithms, as well as information regarding an individual's AV and/or VA conduction profile(s), to identify the source of an arrhythmia exhibiting 1:1 AV conduction as either VT or SVT. Along with automatic updates of an individual's AV and/or VA conduction profiles at times of elevated sympathetic activity, the discrimination algorithm will determine whether an individual experiencing an arrhythmia with 1:1 AV conduction requires defibrillation.

c) Data Collection

One embodiment of the present invention contemplates an ICD that differentiates between SVT and ventricular arrhythmia based on whether the atria or ventricles initiate an electrical signal first following a cessation of anti-tachycardia pacing.

Figure 2:
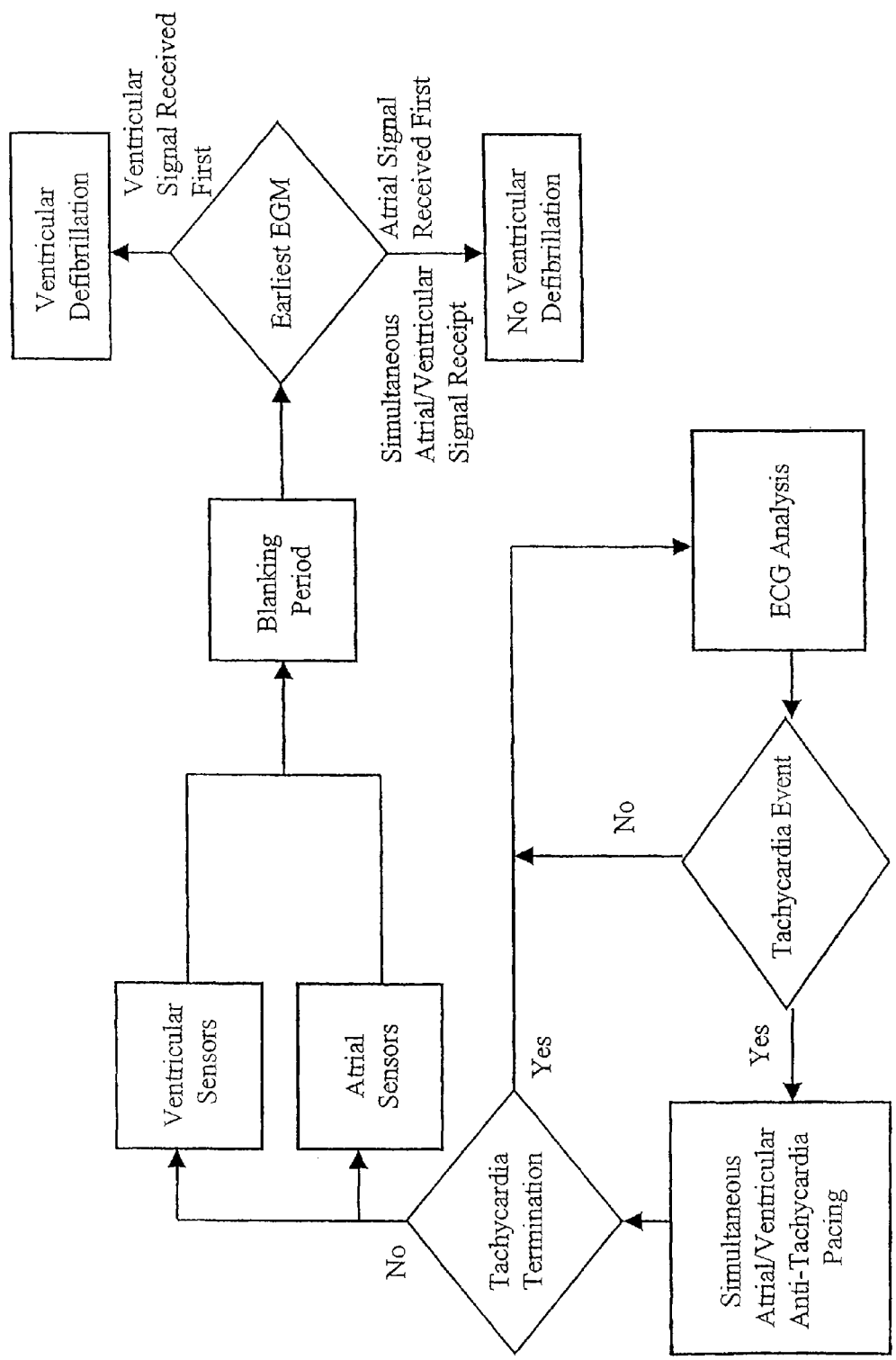
FIG. 2 shows a simplified flowchart of data flow and decision points in one embodiment of discriminating ventricular arrhythmia from SVT and initiation of defibrillation.

FIG. 2 demonstrates how one embodiment of the present invention discriminates between one of three situations below that might be present during abnormal tachycardia:

1. The ventricular electrical activity is sensed prior to the atrial electrical activity: The arrhythmia is originating from the ventricles and, therefore, defibrillation is required.
2. The ventricular electrical activity is sensed after the atrial electrical activity: The arrhythmia is originating from the atria and, therefore, defibrillation is not required.
3. The ventricular electrical activity is sensed almost simultaneously with the atrial electrical activity: This scenario is compatible with a special form of SVT known as atrioventricular nodal reentrant tachycardia which originates from the junction between the atria and ventricles and depolarizes these cardiac chambers almost simultaneously. This form of SVT is not life threatening and therefore defibrillation is inhibited in this situation.

One embodiment of the present invention contemplates an ICD that responds to tachycardia by delivering simultaneous anti-tachycardia pacing bursts (i.e., for example, for a period of, but not limited to, 10 heart beats) to both the atria and ventricles at a cycle length approximately equal to, but not limited to, 80% of the cycle length of the tachycardia. Preferably, the cycle length is modified by altering the ICD programming. In one embodiment, tachycardia is terminated subsequent to the delivery of the anti-tachycardia pacing burst and obviates the need for an immediate origin diagnosis and defibrillation. Preferably, following tachycardia termination the ICD continues to receive EGM activity from both the ventricular and atrial sensing leads. In another embodiment, the ICD maintains storage capability such that all electrical activity sensed from the ventricles and atria are accessible for downloading for later diagnosis of tachycardial events not requiring defibrillation. In another embodiment, tachycardia is not terminated subsequent to the delivery of the anti-tachycardia pacing burst and the ICD then determines whether the atrial channel or the ventricular channel recorded the first electrical activity after a blanking period (i.e., for example, for a length of, but not limited to, 200 msec) following the anti-tachycardia pacing burst. Preferably, the blanking period is modified by altering the ICD programming. In a preferred embodiment, the ICD does not defibrillate if the first sensed electrical activity is atrial (i.e., diagnosed as a SVT). In another preferred embodiment, the ICD does defibrillate if the first sensed electrical activity is ventricular (i.e., diagnosed as a ventricular arrhythmia). In one embodiment, the ICD does not defibrillate upon an almost simultaneous sensing of electrical activity from both the atria and ventricle, wherein said simultaneous electrical activity occurs within, but not limited to, a 60 msec timeframe (i.e., diagnosed as an atrioventricular nodal reentrant tachycardia).

Figure 3:
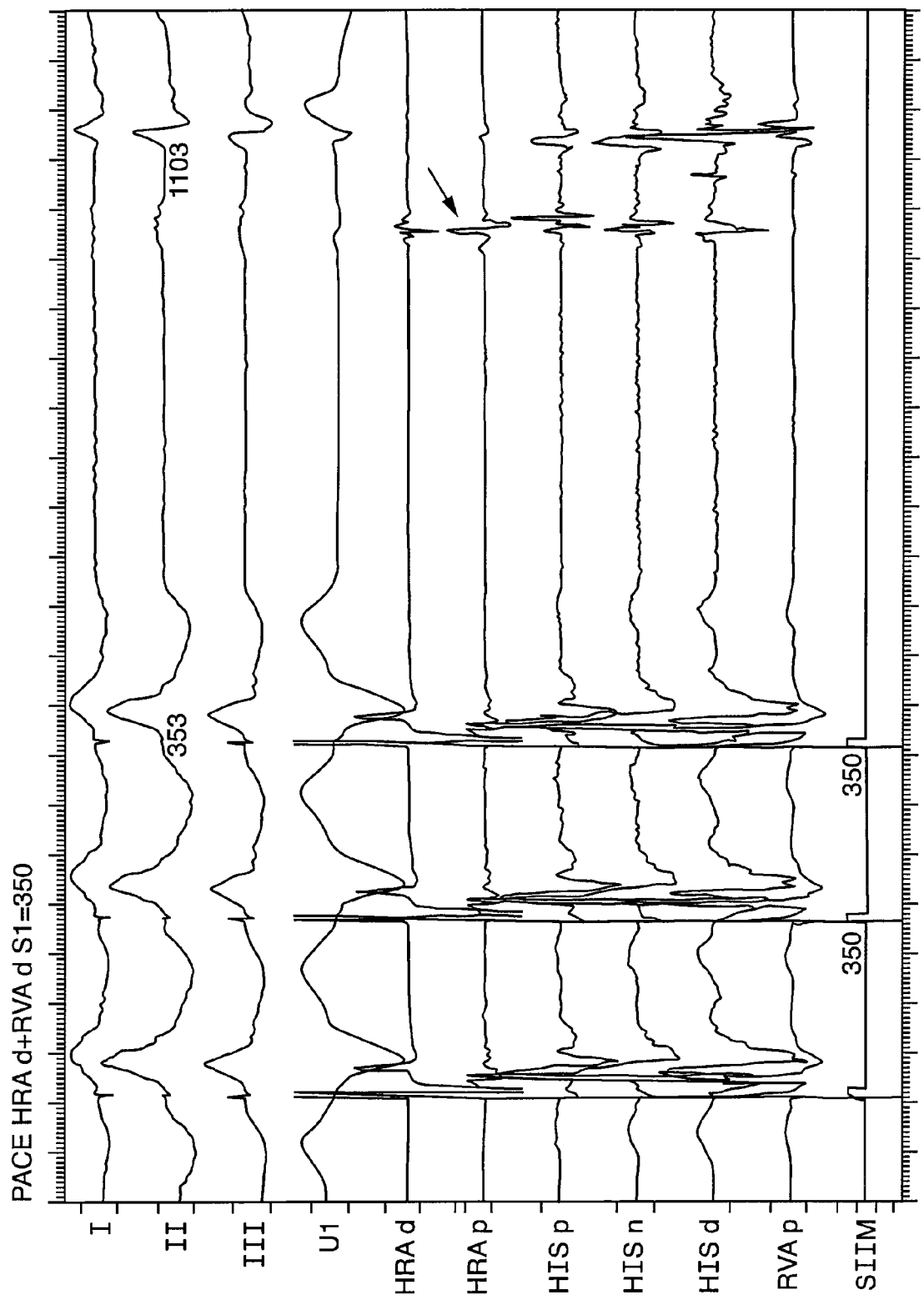
FIG. 3 shows successful termination of tachycardia in a human patient following 350 msec anti-tachycardia pacing bursts.

In another embodiment, simultaneous anti-tachycardia pacing bursts to the atria and ventricles controlled by catheter-inserted quadripole electrodes results in a termination of the existing tachycardia arrhythmia. FIG. 3 depicts the last three pacing square wave beats of 350 msec duration from an anti-tachycardia pacing burst (STIM), where the atrial activation (HRA d and HRA p) is clearly simultaneous with both ventricle activation (RVA p) and His bundle activation (HIS—p, n & d). Following the cessation of the ATP, a normal P-Q-R-S-T profile is visible (arrow) on the HRA p lead, thus indicating a return to normal sinus rhythm.

Figure 4B:
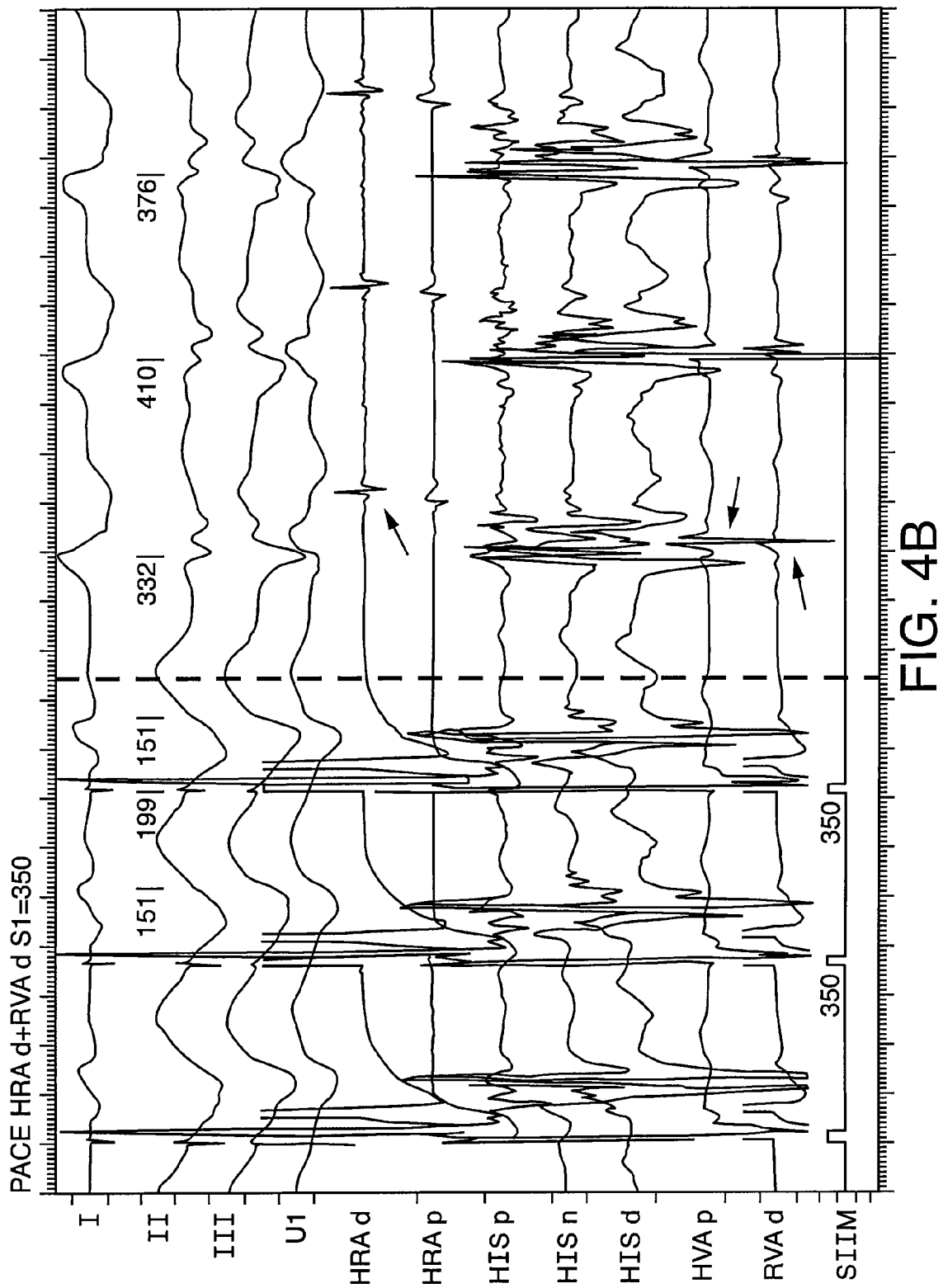
FIG. 4B shows VT persistence in a human patient following 350 msec anti-tachycardia pacing bursts. (blanking period from last ATP stimulation to dashed line)

In another embodiment, simultaneous anti-tachycardia pacing bursts to the atria and ventricles identifies the ventricles as originating the tachycardial event. FIG. 4A shows the last three pacing beats induced by a burst of 400 msec square wave depolarizations (STIM) triggering a blanking period (blanking period from last ATP stimulation to dashed vertical line). After the blanking period, ventricular activity is recorded (see RVA d; arrow) prior to atrial activity (see MAP d; arrow). Similarly, FIG. 4B also shows first arriving ventricular activity except that the pacing beats were induced by 350 msec stimulus (STIM) and atrial activation is recorded on HRA d (see arrow) and HRA p leads and compared with ventricular data recorded on RVA p and RVA d leads (see arrows). Ventricular tachycardia (VT) is diagnosed as persistent in both tracings because the ventricular electrical signal appears prior to the atrial electrical signal during the blanking period.

Figure 5:
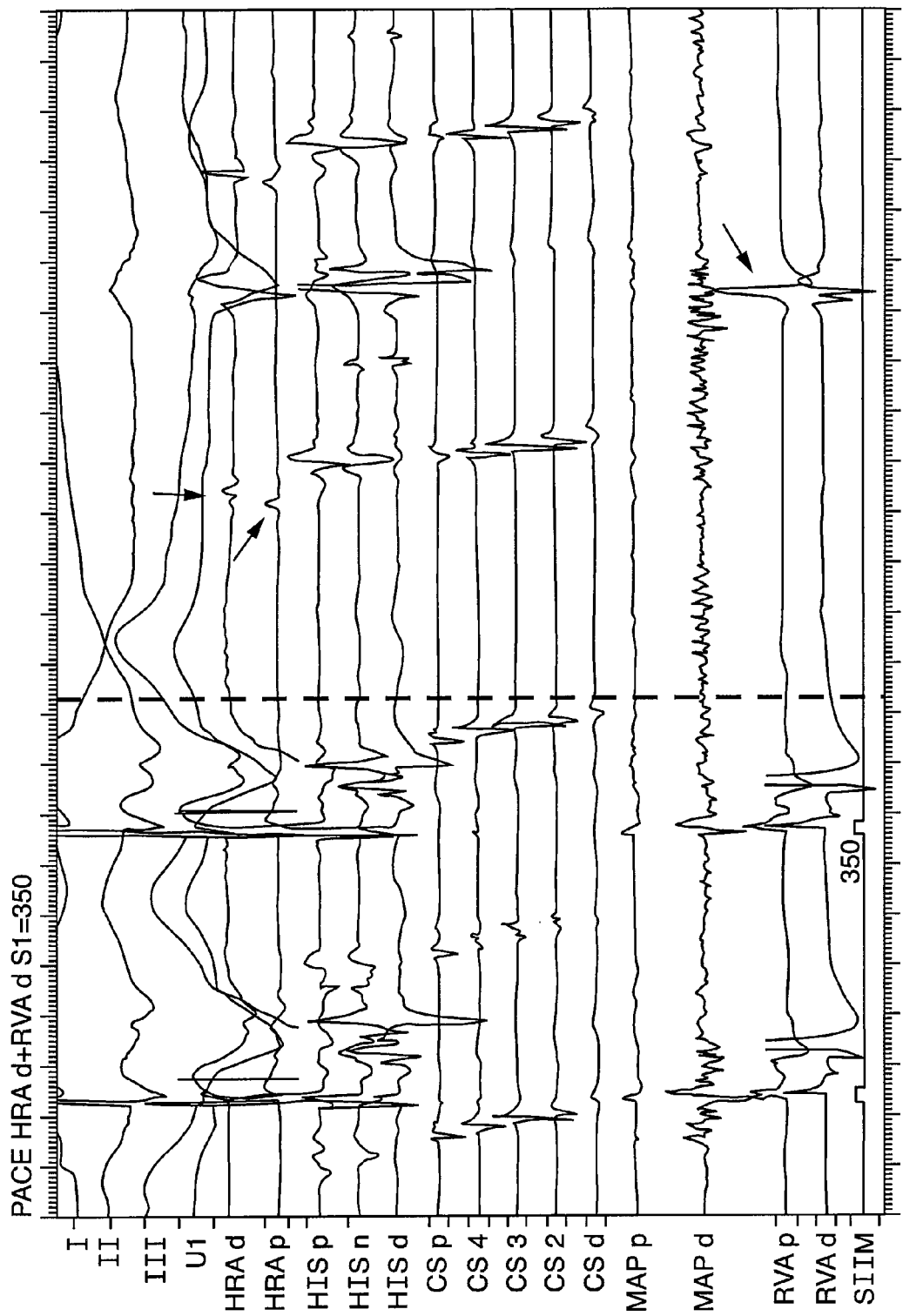
FIG. 5 shows atrial tachycardia persistence in a human patient following 350 msec anti-tachycardia pacing bursts. (blanking period from last ATP stimulation to dashed line)

In another embodiment, simultaneous anti-tachycardia pacing bursts to the atria and ventricles identifies the atria as originating the tachycardial event. FIG. 5 shows the last two pacing beats induced by a 350 msec stimulus (STIM) triggering a blanking period (blanking period from last ATP stimulation to dashed vertical line). After the blanking period, atrial activity is recorded (see HRA d or HRA p; arrows) prior to ventricular activity (RVA p or RVA d; arrow). Supraventricular tachycardia (SVT) is diagnosed as persistent because the atria electrical signal appears prior to the ventricular electrical signal during the blanking period.

Figure 6:
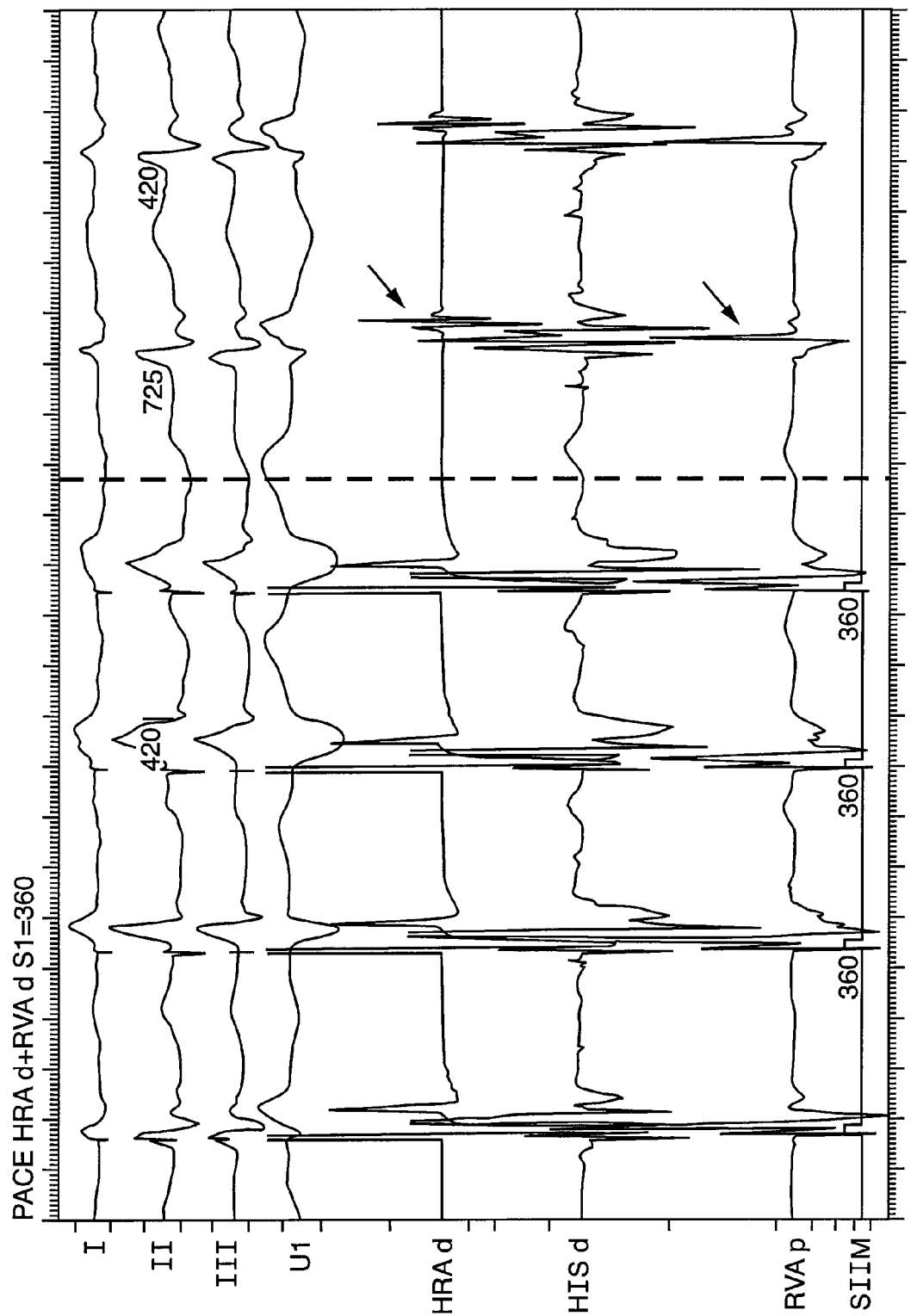
FIG. 6 shows the presence of atrioventricular nodal reentrant tachycardia in a human patient following 360 msec anti-tachycardia pacing bursts. (blanking period from last ATP stimulation to dashed line)

In another embodiment, simultaneous anti-tachycardia pacing bursts to the atria and ventricles identifies the junction between the atria and ventricles as originating the tachycardia event. FIG. 6 shows the last four pacing beats induced by a 360 msec stimulus (STIM) triggering a blanking period (blanking period from last ATP stimulation to dashed vertical line). After the blanking period, atrial activity (HRA d), ventricle activity (RVA p) and His bundle activity (HIS d) all appear simultaneously. Atrioventricular nodal reentrant tachycardia is, therefore, diagnosed.

4) Determination of AV and VA Conduction Rates

It is believed that patients' AV and VA conduction characteristics vary based on their level of activity or their physical and emotional status. Conditions where elevated sympathetic states are present (typically associated with a higher sinus heart rate), may allow AV and/or VA conduction to take place, even when no such condition is present at baseline.

In one embodiment, the present invention contemplates a defibrillator comprising a discrimination algorithm to incorporate and store information about baseline characteristics of atrial to ventricular (AV) and ventricular to atrial (VA) conduction of a patient. Although it is not necessary to understand the mechanism of an invention, it is believed that an operator, presumably an implanting physician, would manually enter information regarding the presence or absence of AV and VA conduction. In another embodiment, an operator, presumably the implanting physician, can update information regarding the presence or absence of AV and VA conduction after the device has been implanted in the patient. An external update of the presence or absence of AV and VA conduction could occur, for example, following the operator/physician's determination that a patient's AV and/or VA conduction profile has changed. In one embodiment, the present invention contemplates that a 1:1 AV conduction rate determined at maximum rate represents an AV Wenckebach (AVW) cycle length. In another embodiment, the present invention contemplates that a 1:1 VA conduction rate determined at maximum rate represents a VA Wenckebach (VAW) cycle length.

In one embodiment, the present invention contemplates a method to determine AV conduction by applying pacing bursts to the atria in short bursts for one or more beats at incrementally faster rates until a corresponding event in the ventricle is no longer sensed. Although it is not necessary to understand the mechanism of an invention, it is believed that this will allow the determination of the presence of AV conduction as well as the level of AVW cycle length in the event AV conduction is present.

In one embodiment, the present invention contemplates a method to determine VA conduction by applying pacing bursts to the ventricle in short bursts for one or more beats at incrementally faster rates until a corresponding event on the atria is no longer sensed. Although it is not necessary to understand the mechanism of the invention, it is believed that this will allow the determination of the presence of VA conduction as well as the level of VAW cycle length in the event VA conduction is present.

In one embodiment, the present invention contemplates that AV and/or VA conduction is determined periodically. In one embodiment, the determination is performed when the sensed atrial rate is elevated denoting a high sympathetic drive. In one embodiment, a smaller value for AVW cycle length is determined, wherein the new minimum AVW value is updated in the algorithm. In one embodiment, a smaller value for VAW cycle length is determined, wherein the new minimum VAW value is updated in the algorithm.

a) Determination of the Origin of a 1:1 Arrhythmia

One embodiment of the present invention contemplates an ICD that differentiates between SVT and VT following an arrhythmia with a 1:1 atrial to ventricular relationship (1:1 AV association). This form of arrhythmia occurs when electrical activity is re-routed through an accessory pathway connecting the atria with the ventricles, resulting in the near simultaneous detection of electrical activity in the atria and ventricles. Two types of tachycardia fall under this category: Antegrade Reentrant Tachycardia (atrioventricular nodal reentrant tachycardia) and Retrograde Reentrant Tachycardia. Antegrade Reentrant Tachycardia is a non life-threatening form of SVT and therefore defibrillation is not required. Retrograde Reentrant Tachycardia is a life-threatening form of VT and therefore defibrillation is required.

Figure 11:
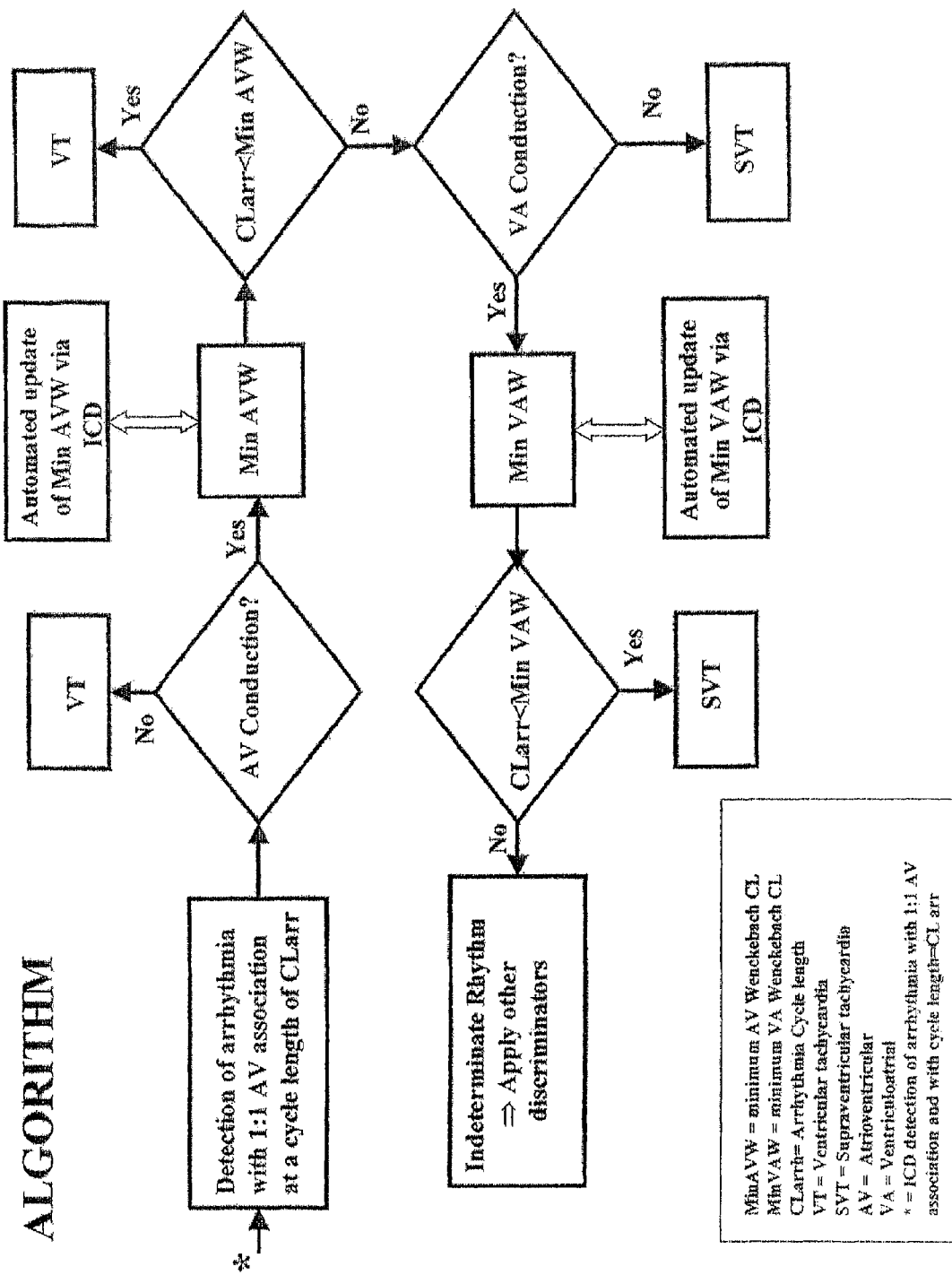
FIG. 11 illustrates one embodiment for a discriminating algorithm providing automatic updates regarding atrioventricular (AV) and ventriculoatrial (VA) conduction rates.
Figure 12:
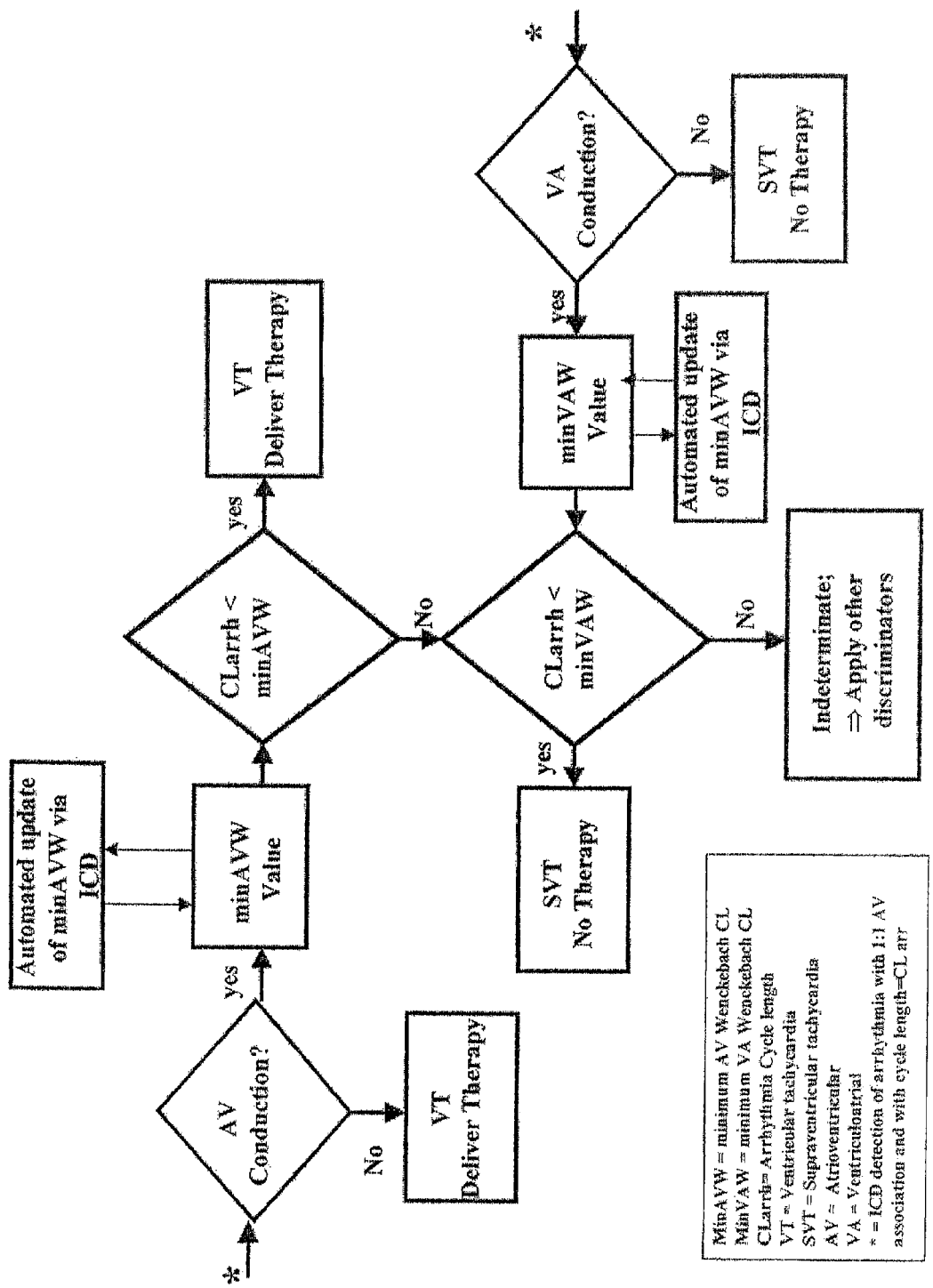
FIG. 12 illustrates one embodiment for a discriminating algorithm providing automatic updates regarding atrioventricular (AV) and ventriculoatrial (VA) conduction rates.
Figure 13:
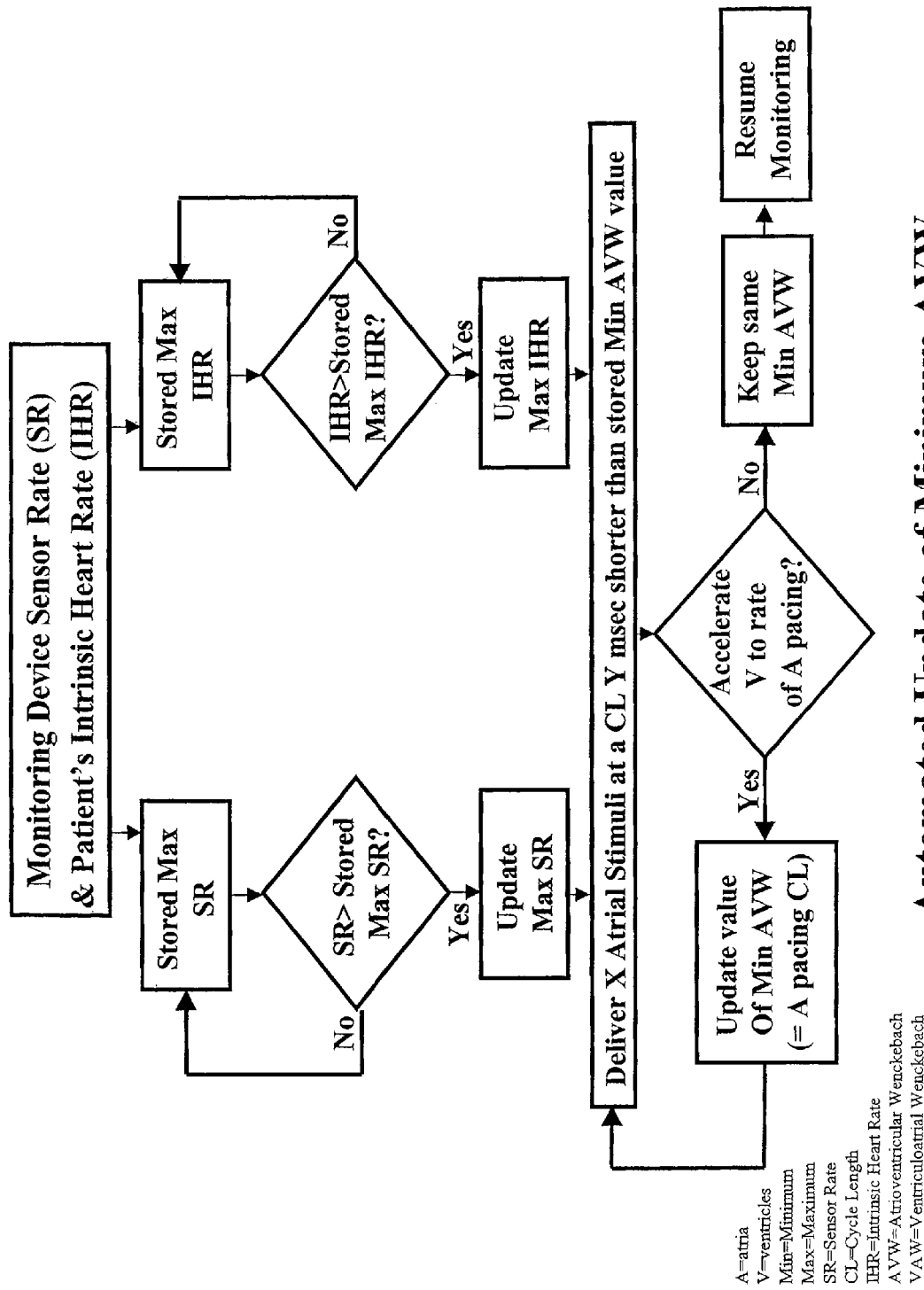
FIG. 13 illustrates one embodiment for a discrimination algorithm providing automatic updates of the minimum AVW cycle length occurring at times of elevated sympathetic activity.
Figure 14:
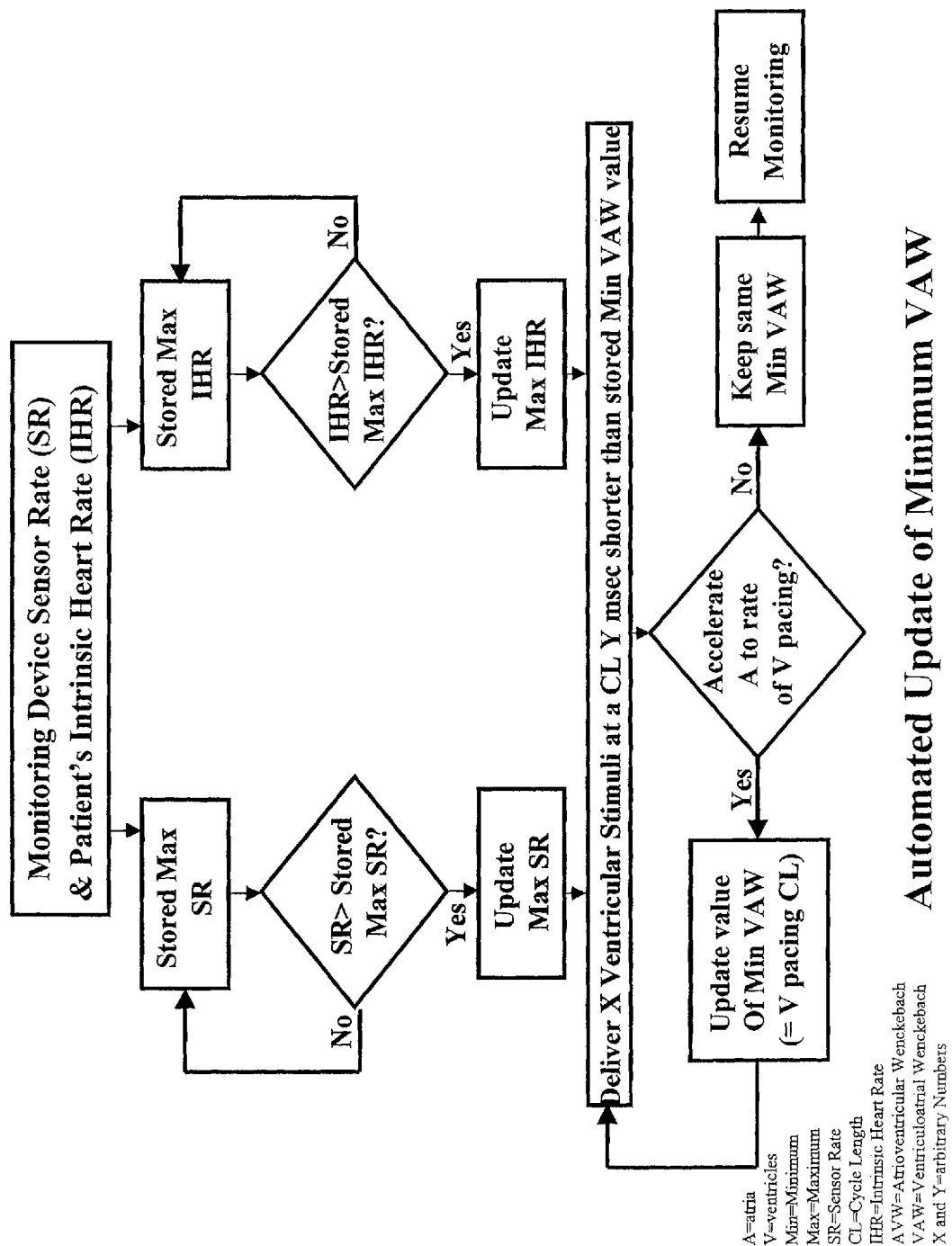
FIG. 14 illustrates one embodiment for a discrimination algorithm providing automatic updates of the minimum VAW cycle length occurring at times of elevated sympathetic activity.

FIG. 11 demonstrates one embodiment of the algorithm used by the ICD to discriminate between SVT and VT following an arrhythmia with 1:1 AV association.

One embodiment of the present invention contemplates an algorithm that determines the origin of an arrhythmia with a 1:1 AV association as SVT or VT.

In one embodiment, the present invention contemplates detecting an arrhythmia with 1:1 AV association in a patient lacking AV conduction. This patient is diagnosed as having VT, and the ICD does defibrillate.

In one embodiment, the present invention contemplates detecting an arrhythmia with 1:1 AV association in a patient with AV conduction. In a preferred embodiment, the ICD determines the AVW cycle length of the arrhythmia. In a preferred embodiment, the algorithm updates the minimum AVW cycle length. In another preferred embodiment, if the cycle length of the arrhythmia with 1:1 AV association is less than the minimum AVW cycle length, the patient is diagnosed as having VT, and the ICD does defibrillate.

In one embodiment, the present invention contemplates detecting an arrhythmia with 1:1 AV association in a patient with AV conduction. In a preferred embodiment, the ICD determines the AVW cycle length of the arrhythmia. In a preferred embodiment, the algorithm updates the minimum AVW cycle length. In another preferred embodiment, if the cycle length of the arrhythmia with 1:1 AV association greater than the minimum AVW cycle length, the ICD determines the minimum VAW cycle length. If the cycle length of the arrhythmia with 1:1 AV association is less than the minimum VAW cycle length, the patient is diagnosed as having SVT, and the ICD does not defibrillate.

In one embodiment, the present invention contemplates detecting an arrhythmia with 1:1 AV association in a patient lacking VA conduction. This patient is diagnosed as having SVT, and the ICD does not defibrillate.

In one embodiment, the present invention contemplates detecting an arrhythmia with 1:1 AV association in a patient with VA conduction. In a preferred embodiment, the ICD determines the VAW cycle length of the arrhythmia. In a preferred embodiment, the algorithm updates the minimum VAW cycle length. In a preferred embodiment, if the cycle length of the arrhythmia with 1:1 AV association is less than the minimum VAW cycle length, the patient is diagnosed as having SVT, and the ICD does not defibrillate.

EXPERIMENTAL

The following are examples that further illustrate embodiments contemplated by the present invention. It is not intended that these examples provide any limitations on the present invention.

EXAMPLE I

Anti-Tachycardia Pacing Responses in Patients Exhibiting Supraventricular Tachycardia and Ventricular Tachycardia This example provides data collected during an electrophysiological testing study demonstrating the effectiveness of anti-tachycardia pacing bursts in patients exhibiting SVT or VT.

A total of twelve patients (three female and nine male) were tested having a mean age of 61+−19 years. A summary breakdown of the patients by characteristics and response to anti-tachycardia pacing for patients is shown in Table 1 below:

TABLE 1

Summary Patient Data For Electrophysiological Testing Study

|  | SVT | VT |
| --- | --- | --- |
| Number of Patients | 8 | 4 |
| Age (years) | 59 +/− 21 | 65 +/− 16 |
| % Female | 37 | 0 |
| Left Ventricular Ejection Fraction (%) | 52 +/− 11 | 32 +/− 10* |
| % Having Cardiac Disease |  |  |
| None | 75 | 0 |
| CAD | 25 | 100 |
| Reason for Electrophysiological Study |  |  |
| SVT | 4 | 0 |
| VT | 0 | 4 |
| Other (syncope, palpitation etc) | 4 | 0 |
| Number of ATP bursts per patient | 6.0 +/− 4.1 | 8.7 +/− 4.7 |
| % Termination per paient | 44 +/− 33 | 17 +/− 22 |

*p < 0.02

The combined average left ventricular ejection fraction was 45+−14% but there was a significant difference between the eight patients diagnosed as having supraventricular tachycardia (SVT: 52+−11%) versus the four patients diagnosed as having ventricular tachycardia (VT: 32+−10%). Of the four VT patients all had a previous history of cardiac disease. However, only two of the eight SVT patients reported any previous history of cardiac disease. The remaining four of the SVT patients presented with symptoms such as syncope or palpitations.

Patients were tested in the fasting state and under conscious sedation (0.5 2 mg Midazolam). Lidocaine (1%) was used for local anesthesia while venous sheaths (6 Fr or 7 Fr) were inserted into the femoral veins. Quadripolar (5 mm interelectrode distance and 1.5 mm electrode thickness) were inserted into the venous sheaths and coursed into the high right atrial, His bundle and right ventricular apical positions that were verified by fluoroscopy observation.

Comparisons of continuous variables between groups were performed using the Student t-test. Discrete variables were compared using Fisher's exact test. A p value<0.05 was considered to be statistically significant.

Catheters were connected to a recording system and a stimulator (EPMed System, NY) via a junction box. If an arrhythmia was induced during the course of the electrophysiologic study and the patient remained hemodynamically stable, then attempts at terminating the arrhythmia using antitachycardia pacing (ATP) bursts were performed. The ATP bursts were delivered from the external stimulator by simultaneous pacing of the atrium and ventricle at a rate corresponding to approximately 80% of the arrhythmia cycle length. The response of the arrhythmia to ATP was then recorded. ATP bursting continued until the arrhythmia terminated or the patient became hemodynamically unstable, at which time the arrhythmia was terminated by external cardioversion (i.e., full-body electroshock).

The arrhythmias were classified as VT or SVT by the attending electrophysiologist based on guidelines well known in the art. Analysis of the response of the arrhythmia to ATP bursting was noted, as well as the earliest electrical recording (i.e., whether recorded on atrial sensing leads or ventricular sensing leads). Responses were classified in one of the following categories:

1) Termination of Arrhythmia: This response is exemplified in FIG. 3. No further electrogram (EGM) activity analysis was performed.
2) Ventricular Tachycardia (VT) Persistence: This response is exemplified in FIGS. 4A and 4B. During the blanking period, the earliest EGM activity was recorded by the ventricular sensing leads.
3) Supraventricular Tachycardia (SVT) Persistence: This response is exemplified in FIG. 5. During the blanking period, the earliest EGM activity was recorded by the atrial sensing leads.
4) Atrioventricular Nodal Reentrant Tachycardia Persistence: This response is exemplified in FIG. 6. During the blanking period, the earliest EGM activity was simultaneously recorded (i.e., within 50 to 60 msec) on both the atrial and ventricular sensing leads. However, for the purposes of the present example only, this condition was diagnosed as a SVT arrhythmia.

Anti-tachycardia pacing bursts were initiated a total of eighty-three times between the twelve patients. The SVT group experienced forty-eight pacing bursts (6.0+/−4.1 per patient) while VT group experienced thirty-five pacing bursts (8.7+/−4.7 per patient). Following twenty-two of the anti-tachycardia pacing bursts, the tachycardia was terminated, while the tachycardia persisted following the remaining sixty-one bursts. The computer algorithm correctly discriminated the first arriving cardiac electrical signal in all sixty-one of the persisting tachycardias and properly diagnosed twenty-nine persisting tachycardias as supraventricular and thirty-two persisting tachycardias as ventricular.

As such, this protocol results in a 100% sensitivity and a 100% specificity and demonstrates one example of a capability of detecting a first arriving electrical signal that discriminates extremely well between VT and SVT.

EXAMPLE II

Anti-Tachycardia Pacing in an Experimental Mouse Model

This example demonstrates that the mouse may be utilized as an experimental model to study earliest arriving electrical activities following anti-tachycardia pacing to identify the source of cardiac tachycardia.

Female FVB mice were anesthetized with xylazine and ketamine (IP) coadminstered with propranolol to reduce the intrinsic heart rate. Under a Nikkon surgical microscope, a 1.7 French octapolar catheter (NuMed Inc., Hopkinton, N.Y.) was introduced through the right jugular vein coursing into the right atrium and right ventricle of the mouse. The electrode spacing on the catheter tip is 0.5 mm and the electrode thickness is 0.5 mm. A six lead surface electrogram was obtained from the mouse by placing one subcutaneous electrode into each limb of the mouse, for a total of four. The surface electrograms were filtered at 0.01 Hz to 100 Hz, and intracardiac signals sampled at 1 KHz, amplified and filtered at 30 to 500 Hz (Labsystem Duo Bard Electrophysiology, Lowell, Mass.).

Demand pacing was achieved by using a single chamber Preva SR pacemaker (Medtronics Inc., Minneapolis, Minn.) set to pace at a very fast rate (up to 400 beats per minute) in temporary mode. The bipolar output of the pacemaker was connected by alligator clips to the proximal pins of the intracardiac catheter for atrial pacing and the distal pins for ventricular pacing. The catheter was also connected to an external stimulator (Bloom Associates Ltd., Reading, Pa.) configured to pace simultaneously the atria and ventricles of the mouse thorough the proximal and distal pins, respectively.

Figure 7:
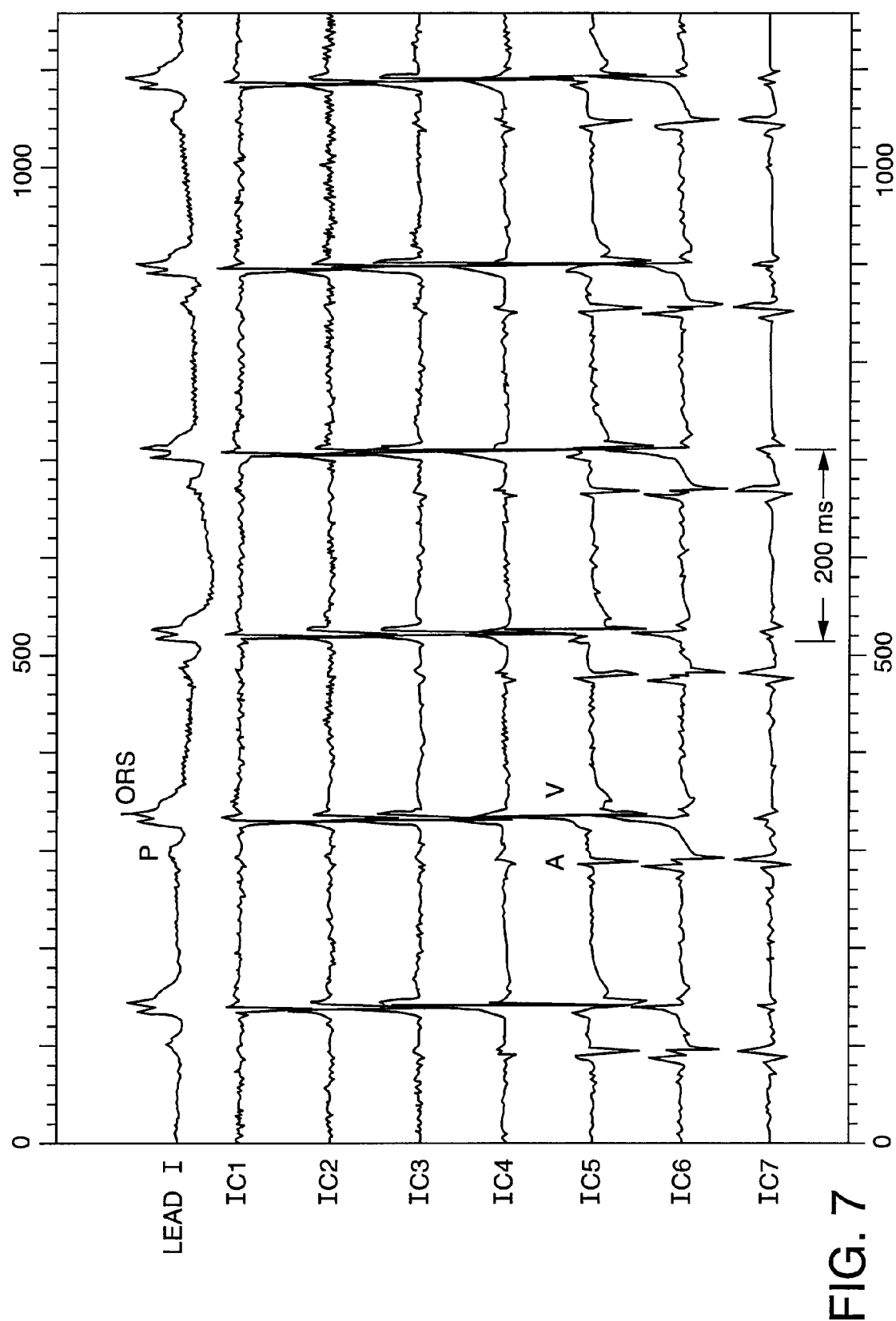
FIG. 7 shows an exemplary normal sinus rhythm tracing in a mouse.

The proper placement of the catheter was verified by the collection an analysis of a normal sinus rhythm. FIG. 7 illustrates a mouse ECG having a normal P-Q-R-S pattern on the surface channel (Lead I) at a cardiac cycle length of approximately 180 to 200 msec (320 to 300 beats per minute). Note that on the intracardiac channels (see, for example, IC5), the A and V electrograms correspond to the P and QRS complexes on the surface electrogram, respectively. Specifically, note that atrial EGM activity (A) occurs prior to ventricular EGM activity (V), as expected in sinus rhythm.

Figure 8:
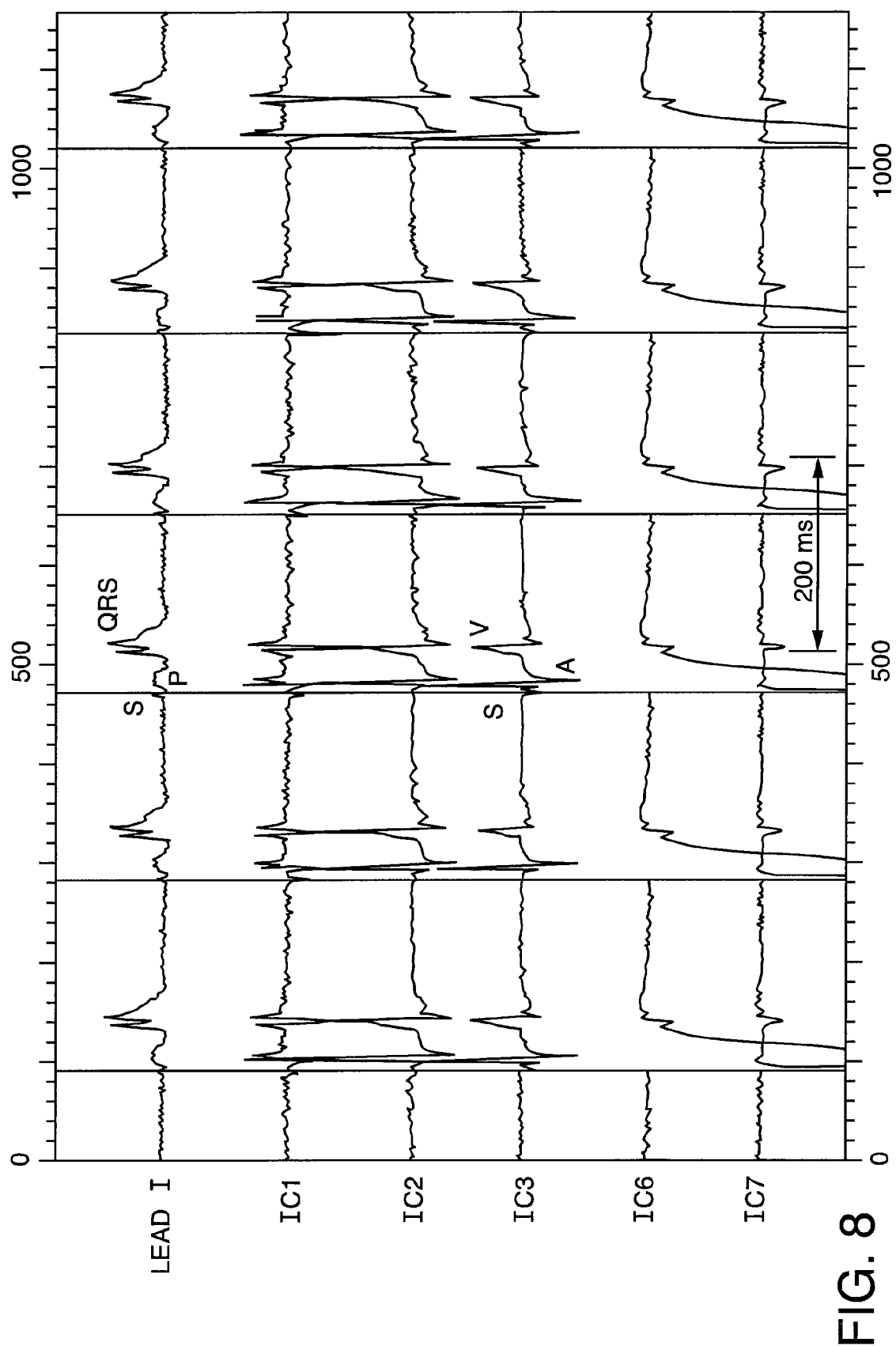
FIG. 8 shows ECG recordings using an octapolar catheter during atrial pacing using a Preva SR pacemaker in a mouse.

FIG. 8 illustrates atrial pacing stimuli (S) at a cycle length of 180 to 200 msec (approximately 320 to 300) beats per minute to simulate a SVT. The vertical black lines indicate the pacing stimulus (S) followed by the atrial EGM (A) and the ventricular EGM (V), annotated in Lead IC3. Similar to the normal sinus rhythm data shown in FIG. 7, Lead IC3 of FIG. 8 shows the normal electrocardiogram sequence, with atrial EGM activity (A) occurring prior to ventricular EGM activity (V). Also, the surface P-Q-R-S complex (Lead I) is similar to that of the normal sinus rhythm tracing seen in FIG. 7.

Figure 9:
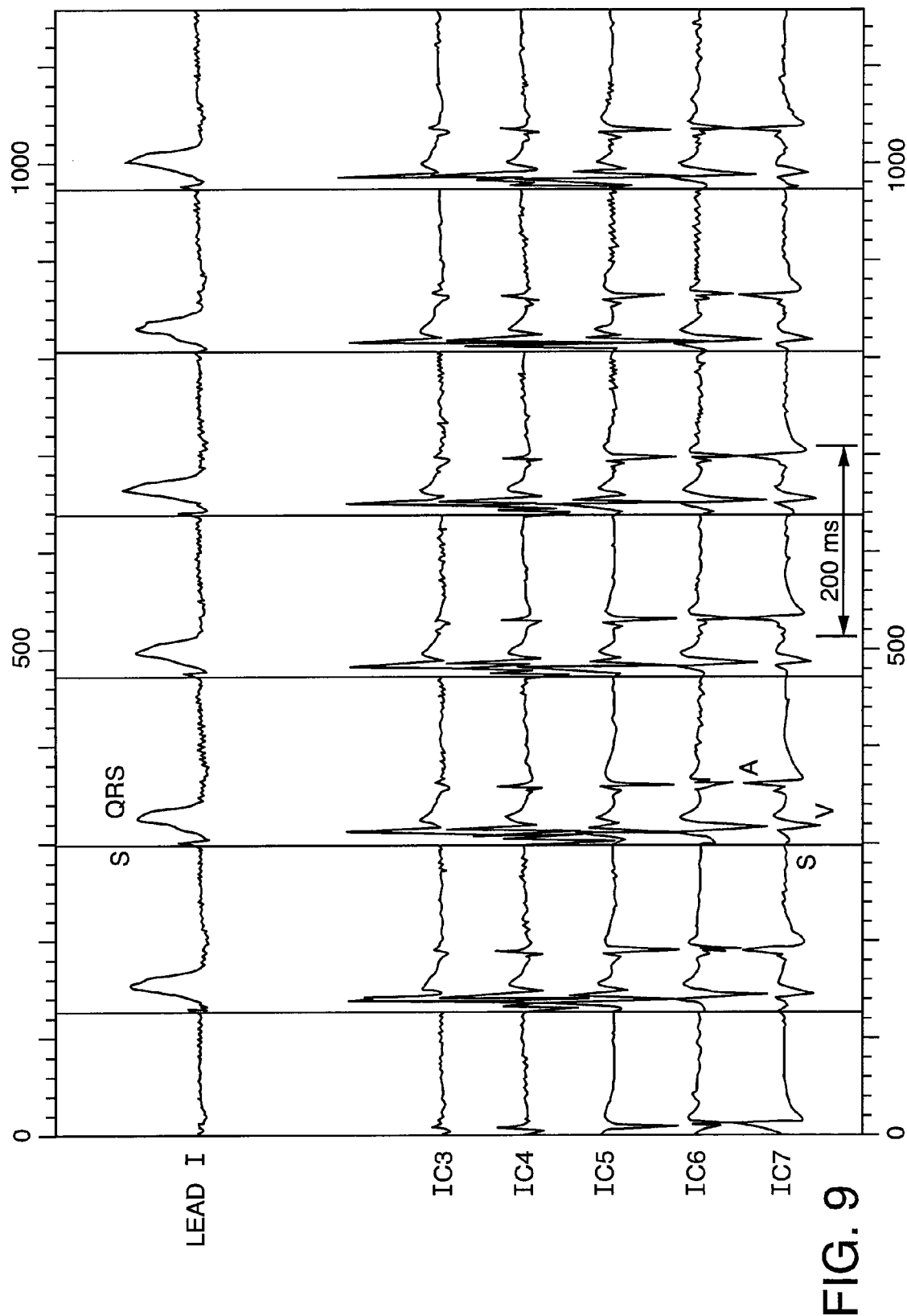
FIG. 9 shows ECG recordings using an octapolar catheter during ventricular pacing using a Preva SR pacemaker in a mouse.

FIG. 9 shows ventricular pacing stimuli (S) at a cycle length of 160 to 180 msec (approximately 375 to 320 beats per minute), to simulate VT. The vertical black lines indicate the pacing stimulus (S) followed by the P-Q-R-S response pattern, annotated in Lead IC7. Contrary to the above data in FIGS. 7 and 8, Lead IC7 of FIG. 9 shows a reversal of the usual P-Q-R-S complex. Specifically, ventricular EGM activity (V) occurs first, followed by atrial EGM activity (A). Also, note that the surface P-Q-R-S pattern (Lead I) during ventricular pacing is different than during sinus rhythm and atrial pacing (see FIGS. 7 & 8, respectively).

Figure 10:
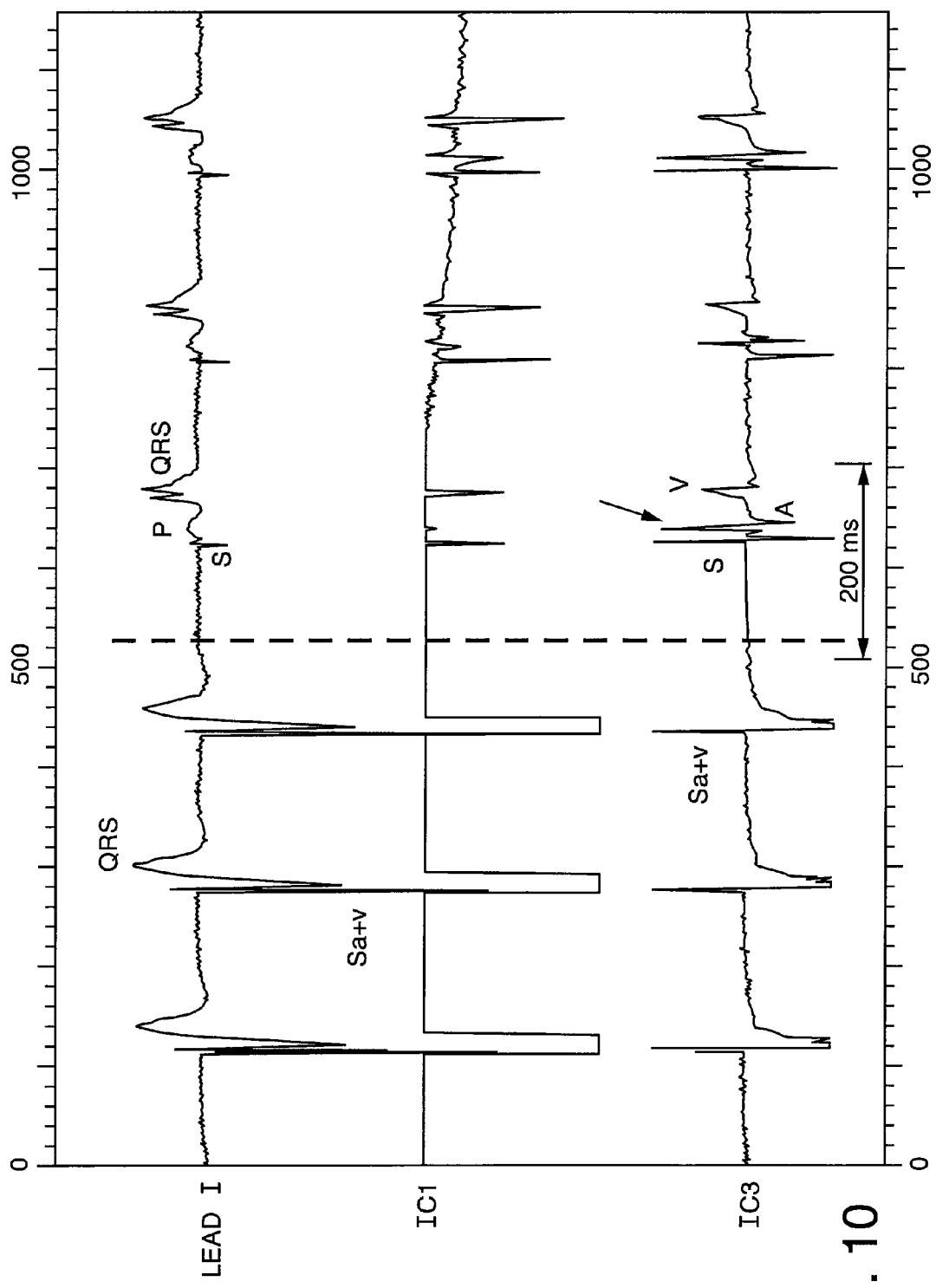
FIG. 10 provides an ECG recording using an octapolar catheter illustrating that atrial activity is the earliest electrical activity following an anti-tachycardia pacing burst during a simulated SVT by atrial pacing.

FIG. 10 shows an exemplary tracing of the earliest arriving electrical activity after ATP on the atrial channel following at least one simultaneous atrial and ventricular anti-tachycardia pacing (ATP) burst of up to 12 beats per burst with a cycle length of 150 to 160 msec (approximately 400 to 375 beats per minute). During simultaneous atrioventricular ATP bursting, the pacemaker output simulating the SVT was inhibited. After the last beat of simultaneous atrioventricular ATP (Lead IC3; Sa+v: arrow), and an approximate 75 to 100 msec blanking period, the earliest electrical activity recorded was atrial EGM activity (A). Note that pacemaker stimulus (S) resumed following the cessation of ATP bursting and prior to the first arriving atrial EGM activity.

In summary, sixty-nine ATP bursts were delivered in two mice, forty-five during atrial pacing and twenty-four during ventricular pacing. The earliest electrical activity after ATP was detected on the atrial channel in all forty-five atrial pacing attempts. Similarly, the earliest electrical activity after ATP was detected on the ventricular channel in all twenty-four ventricle pacing attempts.

As such, this protocol results in a 100% sensitivity and a 100% specificity and demonstrates one capability of detecting a first arriving electrical signal that discriminates extremely well between VT and SVT.

EXAMPLE III

Automated Assessment of Atrioventricular and Ventriculoatrial Conduction

Two separate research studies are currently being designed to test embodiments contemplated by the present invention. The first study is directed towards an acute research protocol in an electrophysiology (EP) laboratory. The second study involves a chronic protocol that requires follow-up studies on patients for up to a year.

Acute Protocol

Patients presenting to the EP laboratory for EP testing or ablation will undergo assessment of AV and VA conduction by pacing the atria and ventricles, respectively, at baseline and then after administration of adrenergically-stimulating agents such as isoproterenol and epinephrine. The minimum cycle length (CL) of pacing under these conditions that results in 1:1 conduction to the opposite chamber will determine the minimum AV and VA Wenckebach CL (min AVW and min VAW, respectively).

Patients will then be induced into ventricular (VT) or supraventricular (SVT) arrhythmias, as per the clinical indication of the EP testing. Once an arrhythmia is induced, the CL of the arrhythmia will be compared to the values of the min AVW and VAW in order to determine how often the proposed method of discrimination would have correctly classified the arrhythmia as VT or SVT. Endpoints of this study will be the sensitivity for detecting VT, the specificity of rejecting SVT, and the positive and negative predictive values of the algorithm.

Chronic Protocol

Patients presenting to the EP laboratory for dual-chamber defibrillator (ICD) or pacemaker (PM) implantation will undergo assessment of AV and VA conduction by pacing the atria and ventricles, respectively, at baseline and then after administration of adrenergically-stimulating agents such as isoproterenol and epinephrine. The minimum cycle length (CL) of pacing under these conditions that results in 1:1 conduction to the opposite chamber will determine the minimum AV and VA Wenckebach CL (min AVW and min VAW, respectively).

Patient will then be discharged and followed as per standard of care in the device clinic where periodic assessment of any arrhythmic events will be performed. In the event of arrhythmia detection, the CL of the arrhythmia will be compared to the values of the min AVW and VAW in order to determine how often the proposed method of discrimination would have correctly classified the arrhythmia as VT or SVT. The endpoints of this study will be the sensitivity for detecting VT, the specificity of rejecting SVT, and the positive and negative predictive values of the algorithm.

EXAMPLE IV

Automatic Update of Minimum AVW and VAW

The following equations, representing the steps for automatically updating minimum AVW and VAW values, are written in simple BASIC format but could be adapted to any other computer language.

TABLE 1

Automatic Update Of Minimum AVW

| Step | Function | Definition |
|---|---|---|
| 10 | Input X | Minimum AVW entered at device implantation or interrogation |
| 20 | Input T | Decrement in cycle length of pacing (may vary from 1 to 20 msec) |
| 30 | S=X | |
| 40 | Pace Atrium at cycle length S | Initiate pacing iterations at previously stored value of Minimum AVW |
| 50 | If Atrial pacing results in 1:1 AV relationship then S=S−T | Decrease S by decremental value T |
| 60 | Go To 40 | |
| 70 | X=S | Updated value of minimum AVW |

Implementation of the above equation occurs when at least one of two conditions are met: 1) A pacing burst generated by atrial pacing leads, having a cycle length equal to a previously determined minimum AVW cycle length, no longer represents the minimum cycle length capable of producing a 1:1 AV relationship when detected by ventricular sensing lead(s) and/or, 2) The patient experiences an elevated sympathetic state.

Either of the above scenarios results in atrial pacing lead(s) generating a new series of decremental pacing bursts (S=S−T) to re-establish the minimum AVW cycle length capable of producing a 1:1 AV relationship. Each time an updated value of minimum AVW cycle length (S) is determined, that value is stored in a microprocessor at memory site X (X=S).

TABLE 2

Automatic Update Of Minimum VAW

| Step | Function | Definition |
|---|---|---|
| 10 | Input Y | Minimum VAW entered at device implantation or interrogation |
| 20 | Input M | Decrement in cycle length of pacing (may vary from 1 to 20 msec) |
| 30 | N=Y | |

TABLE 2-continued

Automatic Update Of Minimum VAW

| Step | Function | Definition |
|---|---|---|
| 40 | Pace Ventricle at cycle length N | Initiate pacing iterations at previously stored value of Minimum VAW |
| 50 | If Ventricular pacing results in 1:1 VA relationship then N=N−M | Decrease N by decremental value M |
| 60 | Go To 40 | |
| 70 | Y=N | Updated value of minimum VAW |

Implementation of the above equation occurs when at least one of two conditions are met: 1) A pacing burst generated by ventricular pacing leads, having a cycle length equal to a previously determined minimum VAW cycle length, no longer represents the minimum cycle length capable of producing a 1:1 AV relationship when detected by atrial sensing lead(s) and/or, 2) The patient experiences an elevated sympathetic state.

Either of the above scenarios results in ventricular pacing lead(s) generating a new series of decremental pacing bursts (N=N−M) to re-establish the minimum VAW cycle length capable of producing a 1:1 AV relationship. Each time an updated value of minimum VAW cycle length (N) is determined, that value is stored in a microprocessor at memory site Y (Y=N).

Following detection of an arrhythmia with a 1:1 relationship, the cycle length (CL) of the arrhythmia is compared to the values stored at memory sites X and Y (Tables 1 and 2, respectively). These values, along with data previously entered by an operator/implanting physician concerning an individual patient's AV and/or VA conduction status, are applied to a discrimination equation to identify the origin of the arrhythmia as supraventricular (SVT) or ventricular (VT). The resulting diagnosis dictates whether or not life-saving defibrillation is administered.

TABLE 3

Discrimination Equation

| Step | Function | Status/Response |
|---|---|---|
| 10 | Input AV conduction status | Is patient capable of AV conduction (Yes/No) |
| 20 | Input VA conduction status | Is patient capable of VA conduction (Yes/No) |
| 30 | Input X (Table 1) | Updated value of minimum AVW |

TABLE 3-continued

Discrimination Equation

| Step | Function | Status/Response |
|---|---|---|
| 40 | Input Y (Table 2) | Updated value of minimum VAW |
| 50 | Determine Cycle Length (CL) of Arrhythmia with a 1:1 Relationship | |
| 60 | If Step 10=No | Diagnose VT (Defibrillate) |
| 70 | If Step 20=No | Diagnose SVT (Do Not Defibrillate) |
| 80 | If Step 10=Yes and CL<X | Diagnose VT (Defibrillate) |
| 90 | If Step 20=Yes and CL<Y | Diagnose SVT (Do Not Defibrillate) |
| 100 | If Step 10=Yes and If CL>X but CL<Y | Diagnose SVT (Do Not Defibrillate) |

The ability to automatically monitor, update, and store minimum AVW and VAW cycle length values, together with baseline information of cardiac conduction profiles, ensures individually tailored high-resolution discrimination between SVT and VT. The resulting decrease in inappropriate defibrillations not only reduces patient anxiety and discomfort, but also increases ICD battery life.

I claim:

1. A method, comprising:
   a) providing, under conditions so as to generate ventricular QRS complex signals:
      i) a first set of atrial pacing bursts having a first cycle length; and
      ii) a second set of atrial pacing bursts, wherein said second atrial pacing bursts having a second cycle length: and
   b) detecting said ventricular QRS complex signals generated in response to said second set of atrial pacing bursts, wherein said second atrial pacing burst cycle length is shorter than said first atrial pacing burst cycle length;
   c) repeating step b) until said ventricular QRS complex signals are not detected, wherein the penultimate second atrial pacing burst establishes an Atrioventricular Wenckenbach cycle length value.

2. The method of claim 1, further comprising step (d) storing a basal atrioventricular cycle length value in a microprocessor.

3. The method of claim 2, further comprising replacing said basal atrioventricular cycle length value with said Atrioventricular Wenckenbach cycle length value.

4. The method of claim 2, wherein said microprocessor is integrated within a pacemaker/defibrillator device.

\* \* \* \* \*